(12) United States Patent
Chang et al.

(10) Patent No.: US 11,041,021 B2
(45) Date of Patent: Jun. 22, 2021

(54) CAR BASED IMMUNOTHERAPY

(71) Applicant: University of Florida Research Foundation, Inc., Gainesville, FL (US)

(72) Inventors: Lung-Ji Chang, Gainesville, FL (US); Jan S. Moreb, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 961 days.

(21) Appl. No.: 15/312,370

(22) PCT Filed: May 22, 2015

(86) PCT No.: PCT/US2015/032245
§ 371 (c)(1),
(2) Date: Nov. 18, 2016

(87) PCT Pub. No.: WO2015/179801
PCT Pub. Date: Nov. 26, 2015

(65) Prior Publication Data
US 2017/0137515 A1    May 18, 2017

Related U.S. Application Data

(60) Provisional application No. 62/002,603, filed on May 23, 2014.

(51) Int. Cl.
| | | |
|---|---|---|
| *A61K 39/00* | (2006.01) | |
| *C07K 16/28* | (2006.01) | |
| *C07K 16/30* | (2006.01) | |
| *C07K 14/705* | (2006.01) | |
| *C07K 14/725* | (2006.01) | |
| *C12N 5/0783* | (2010.01) | |

(52) U.S. Cl.
CPC ...... *C07K 16/2803* (2013.01); *A61K 39/0011* (2013.01); *A61K 39/00111* (2018.08); *A61K 39/001104* (2018.08); *A61K 39/001112* (2018.08); *A61K 39/001113* (2018.08); *A61K 39/001119* (2018.08); *A61K 39/001124* (2018.08); *A61K 39/001168* (2018.08); *A61K 39/001171* (2018.08); *A61K 39/001186* (2018.08); *A61K 39/001188* (2018.08); *A61K 39/001195* (2018.08); *C07K 14/7051* (2013.01); *C07K 14/70521* (2013.01); *C07K 14/70578* (2013.01); *C07K 16/30* (2013.01); *C12N 5/0638* (2013.01); *A61K 2039/505* (2013.01); *A61K 2039/5158* (2013.01); *C07K 2317/622* (2013.01); *C07K 2319/02* (2013.01); *C07K 2319/03* (2013.01); *C07K 2319/30* (2013.01); *C12N 2510/00* (2013.01)

(58) Field of Classification Search
CPC ...... A61K 2039/5158; A61K 2039/505; A61K 39/0011; A61K 39/001168; A61K 39/001171; A61K 39/001113; A61K 39/001124; A61K 39/001104; A61K 39/00117; C07K 14/7051; C07K 2319/03; C07K 2317/622; C07K 2319/02; C07K 14/70578; C12N 5/0638
See application file for complete search history.

(56) References Cited

U.S. PATENT DOCUMENTS

| | | |
|---|---|---|
| 9,089,520 B2 | 7/2015 | Brenner |
| 10,117,932 B2 | 11/2018 | Shultz et al. |
| 10,647,778 B2 | 5/2020 | Chang |
| 2005/0113564 A1 | 5/2005 | Campana et al. |
| 2013/0280220 A1 | 10/2013 | Ahmed et al. |
| 2014/0301993 A1 | 10/2014 | Powell, Jr. et al. |
| 2014/0322183 A1 | 10/2014 | Milone et al. |
| 2015/0023937 A1 | 1/2015 | Vera Valdes et al. |
| 2015/0118252 A1 | 4/2015 | Ho et al. |
| 2015/0329640 A1 | 11/2015 | Finer |
| 2016/0046724 A1 | 2/2016 | Brogdon et al. |
| 2017/0137515 A1 | 5/2017 | Chang et al. |
| 2017/0226216 A1 | 8/2017 | Morgan et al. |
| 2018/0022815 A1 | 1/2018 | Chang |
| 2018/0142034 A1 | 5/2018 | Chang |
| 2019/0153109 A1 | 5/2019 | Rivkees et al. |

FOREIGN PATENT DOCUMENTS

| | | | |
|---|---|---|---|
| WO | WO 2012/033885 A1 | | 3/2012 |
| WO | WO2012/058460 | * | 5/2012 |
| WO | WO2013/074916 | * | 5/2013 |
| WO | WO 2013/123061 A1 | | 8/2013 |
| WO | WO 2013/126729 A1 | | 8/2013 |
| WO | WO 2014/039523 A1 | | 3/2014 |
| WO | WO 2014/055771 A1 | | 4/2014 |
| WO | WO 2014/055657 A1 | | 10/2014 |
| WO | WO 2015/179801 A1 | | 11/2015 |
| WO | WO 2016/130598 A1 | | 8/2016 |

OTHER PUBLICATIONS

Straathof, K.C. et al. An inducible caspase 9 safety switch for T-cell therapy. Blood, 2005, 105(11):4247-4254).*
International Search Report and Written Opinion dated May 20, 2016 for Application No. PCT/US2016/01721.
International Preliminary Report on Patentability dated Aug. 24, 2017 for Application No. PCT/US2016/017219.
International Search Report and Written Opinion dated Jun. 17, 2016 for Application No. PCT/US2016/018716.
International Preliminary Report on Patentability dated Aug. 31, 2017 for Application No. PCT/US2016/018716.

(Continued)

*Primary Examiner* — Vanessa L. Ford
*Assistant Examiner* — Bruce D. Hissong
(74) *Attorney, Agent, or Firm* — Wolf, Greenfield & Sacks, P.C.

(57) ABSTRACT

The disclosure provides chimeric antigen receptors (CARs), T cells comprising such CARs, nucleic acids that encode such CARS, and methods of use thereof, e.g., to treat cancer such as B cell malignancies.

8 Claims, 13 Drawing Sheets

Specification includes a Sequence Listing.

(56) References Cited

OTHER PUBLICATIONS

International Search Report and Written Opinion dated Sep. 6, 2017 for Application No. PCT/US2017/030279.
International Preliminary Report on Patentability dated Nov. 8, 2018 for Application No. PCT/US2017/030279.
Supplementary European Search Report dated Jun. 12, 2018 for Application No. EP 16749750.2.
Partial Supplementary European Search Report dated Jul. 27, 2018 for Application No. EP 16753166.4.
Supplementary European Search Report dated Nov. 6, 2018 for Application No. EP 16753166.4.
Callahan et al., At the bedside: CTLA-4- and PD-1-blocking antibodies in cancer immunotherapy. J Leukoc Biol. Jul. 2013;94(1):41-53. doi: 10.1189/jlb.1212631. Epub May 10, 2013.
Di Stasi et al., Inducible Apoptosis as a Safety Switch for Adopitce Cell Therapy. The New England Journal of Medicine. Nov. 3, 2011;365(18):1673-83.
Gargett et al., The inducible caspase-9 suicide gene system as a "safety switch" to limit on-target, off-tumor toxicities of chimeric antigen receptor T cells. Frontiers in Pharmacology. Oct. 2014;5:1-7.
Genbank Submission; "AAAT18_RS09785 hypothetical protein [Rhodococcus aetherivorans]", Gene ID: 29568086, updated on Apr. 20, 2017. 2 pages.
Genbank Submission; NIH/NCBI, Accession No. NP_001183.2: "TNFRSF17 TNF receptor superfamily member 17[Homo sapiens]", Gene ID: 608. Last updated on Sep. 30, 2018. 5 pages.
Genbank Submission; NIH/NCBI, Accession No. NP_002988.2: "syndecan-1 precursor [Homo sapiens]", Nov. 5, 2002. 2 pages.
Heczey et al., Invariant NKT cells with chimeric antigen receptor provide a novel platform for safe and effective cancer immunotherapy. Blood. Oct. 30, 2014;124(18):2824-33. doi: 10.1182/blood-2013-11-541235. Epub Jul. 21, 2014.
Highfill et al., Anti-PD1 Therapy for Pediatric Sarcomas. Retrieved from the Internet. http://sarcomahelp.org/research/immuntherapy-pediatric-sarcomas.html#tpm2_1. May 10, 2016.
Lee et al., The future is now: chimeric antigen receptors as new targeted therapies for childhood cancer. Clin Cancer Res. May 15, 2012;18(10):2780-90. doi: 10.1158/1078-0432.CCR-11-1920.
Novak et al., Expression of BCMA, TACI, and BAFF-R in multiple myeloma: a mechanism for growth and survival. Blood. Jan. 2004;103(2):689-694.
Prosser et al., Tumor PD-L1 co-stimulates primary human CD8(+) cytotoxic T cells modified to express a PD1:CD28 chimeric receptor. Mol Immunol. Jul. 2012;51(3-4):263-72. doi: 10.1016/j.molimm.2012.03.023. Epub Apr. 11, 2012.
Rappl et al., The CD3-Zeta Chimeric Antigen Receptor Overcomes TCR Hypo-Responsiveness of Human Terminal LateStage T Cells. PLoS One. 2012;7(1):e30713:1-10.
Sadelain et al., The Basic Principles of Chimeric Antigen Receptor Design. Cancer Discovery. Apr. 2013;3(4):388-98.
Sherbenou et al., The development of potential antibody-based therapies for myeloma. Blood Rev. Mar. 2015;29(2):81-91. doi: 10.1016/j.blre.2014.09.011. Epub Sep. 28, 2014.
Song et al., CD27 costimulation augments the survival and antitumor activity of redirected human T cells in vivo. Blood. Jan. 19, 2012;119(3):696-706. doi: 10.1182/blood-2011-03-344275. Epub Nov. 23, 2011.
Wu et al., The IL-15 receptor α chain cytoplasmic domain is critical for normal IL-15R α function but is not required for trans-presentation. Blood. Sep. 2008;112(12):4411-4419.
International Search Report and Written Opinion dated Sep. 14, 2015 for Application No. PCT/US2015/032245.
International Preliminary Report on Patentability dated Dec. 8, 2016 for Application No. PCT/US2015/032245.
Gill et al., CAR-modified anti-CD19 T cells for the treatment of B-cell malignancies: rules of the road. Expert Opin Biol Ther. Jan. 2014;14(1):37-49. doi: 10.1517/14712598.2014.860442. Epub Nov. 21, 2013.

\* cited by examiner

IVIg ON DAY 19 AFTER CAR INFUSION AND EVERY 3 WEEKS

SEQUENCE LISTING

```
<160> NUMBER OF SEQ ID NOS: 45

<210> SEQ ID NO 1
<211> LENGTH: 5
<212> TYPE: PRT
<213> ORGANISM: Artificial sequence
<220> FEATURE:
<223> OTHER INFORMATION: Spacer

<400> SEQUENCE: 1

Gly Gly Gly Gly Ser
1               5

<210> SEQ ID NO 2
<211> LENGTH: 10
<212> TYPE: PRT
<213> ORGANISM: Artificial sequence
<220> FEATURE:
<223> OTHER INFORMATION: Spacer

<400> SEQUENCE: 2

Gly Gly Gly Gly Ser Gly Gly Gly Gly Ser
1               5                   10

<210> SEQ ID NO 3
<211> LENGTH: 15
<212> TYPE: PRT
<213> ORGANISM: Artificial sequence
<220> FEATURE:
<223> OTHER INFORMATION: Spacer

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 18
<212> TYPE: PRT
<213> ORGANISM: Artificial sequence
<220> FEATURE:
```

<223> OTHER INFORMATION: GS18 spacer

<400> SEQUENCE: 4

Gly Ser Thr Ser Gly Gly Gly Ser Gly Gly Ser Gly Gly Gly Gly
1               5                   10                  15

Ser Ser

<210> SEQ ID NO 5
<211> LENGTH: 18
<212> TYPE: PRT
<213> ORGANISM: Artificial sequence
<220> FEATURE:
<223> OTHER INFORMATION: 218S spacer

<400> SEQUENCE: 5

Gly Ser Thr Ser Gly Ser Gly Lys Pro Gly Ser Ser Glu Gly Ser Thr
1               5                   10                  15

Lys Gly

<210> SEQ ID NO 6
<211> LENGTH: 8
<212> TYPE: PRT
<213> ORGANISM: Artificial sequence
<220> FEATURE:
<223> OTHER INFORMATION: GS8 spacer

<400> SEQUENCE: 6

Gly Gly Gly Gly Ser Gly Gly Gly
1               5

<210> SEQ ID NO 7
<211> LENGTH: 16
<212> TYPE: PRT
<213> ORGANISM: Artificial sequence
<220> FEATURE:
<223> OTHER INFORMATION: Hinge

<400> SEQUENCE: 7

Val Glu Pro Lys Ser Cys Asp Lys Thr His Thr Cys Pro Pro Cys Pro
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: C233S Hinge

<400> SEQUENCE: 8

Leu Asp Pro Lys Ser Ser Asp Lys Thr His Thr Cys Pro Pro Cys Pro
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: C233P Hinge

<400> SEQUENCE: 9

Val Glu Pro Lys Ser Pro Asp Lys Thr His Thr Cys Pro Pro Cys Pro
1               5                   10                  15

<210> SEQ ID NO 10
<211> LENGTH: 11

```
<212> TYPE: PRT
<213> ORGANISM: Artificial sequence
<220> FEATURE:
<223> OTHER INFORMATION: Delta5 Hinge

<400> SEQUENCE: 10

Leu Asp Lys Thr His Thr Cys Pro Pro Cys Pro
1               5                   10

<210> SEQ ID NO 11
<211> LENGTH: 202
<212> TYPE: PRT
<213> ORGANISM: Artificial sequence
<220> FEATURE:
<223> OTHER INFORMATION: CD28 amino acids 19-220

<400> SEQUENCE: 11

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Phe Trp Val Leu Val Val Val Gly Gly Val
    130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
            180                 185                 190

Pro Pro Arg Asp Phe Ala Ala Tyr Arg Ser
        195                 200

<210> SEQ ID NO 12
<211> LENGTH: 27
<212> TYPE: PRT
<213> ORGANISM: Artificial sequence
<220> FEATURE:
<223> OTHER INFORMATION: CD28 transmembrane domain

<400> SEQUENCE: 12

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 13
<211> LENGTH: 109
<212> TYPE: PRT
```

<213> ORGANISM: Artificial sequence
<220> FEATURE:
<223> OTHER INFORMATION: CD28 region

<400> SEQUENCE: 13

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Ala Ser
            100                 105
```

<210> SEQ ID NO 14
<211> LENGTH: 241
<212> TYPE: PRT
<213> ORGANISM: Artificial sequence
<220> FEATURE:
<223> OTHER INFORMATION: CD27 amino acids 20-260

<400> SEQUENCE: 14

```
Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
    130                 135                 140

Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg Ile Leu Val Ile
                165                 170                 175

Phe Ser Gly Met Phe Leu Val Phe Thr Leu Ala Gly Ala Leu Phe Leu
            180                 185                 190

His Gln Arg Arg Lys Tyr Arg Ser Asn Lys Gly Glu Ser Pro Val Glu
        195                 200                 205

Pro Ala Glu Pro Cys His Tyr Ser Cys Pro Arg Glu Glu Glu Gly Ser
    210                 215                 220
```

```
Thr Ile Pro Ile Gln Glu Asp Tyr Arg Lys Pro Glu Pro Ala Cys Ser
225                 230                 235                 240

Pro

<210> SEQ ID NO 15
<211> LENGTH: 48
<212> TYPE: PRT
<213> ORGANISM: Artificial sequence
<220> FEATURE:
<223> OTHER INFORMATION: CD8 hinge domain

<400> SEQUENCE: 15

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Cys Asp
            35                  40                  45

<210> SEQ ID NO 16
<211> LENGTH: 48
<212> TYPE: PRT
<213> ORGANISM: Artificial sequence
<220> FEATURE:
<223> OTHER INFORMATION: CD27 signaling domain

<400> SEQUENCE: 16

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
            35                  40                  45

<210> SEQ ID NO 17
<211> LENGTH: 42
<212> TYPE: PRT
<213> ORGANISM: Artificial sequence
<220> FEATURE:
<223> OTHER INFORMATION: CD137 signaling domain

<400> SEQUENCE: 17

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 18
<211> LENGTH: 41
<212> TYPE: PRT
<213> ORGANISM: Artificial sequence
<220> FEATURE:
<223> OTHER INFORMATION: CD28 signaling domain

<400> SEQUENCE: 18

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
```

```
                35                  40

<210> SEQ ID NO 19
<211> LENGTH: 112
<212> TYPE: PRT
<213> ORGANISM: Artificial sequence
<220> FEATURE:
<223> OTHER INFORMATION: CDzeta signaling domain

<400> SEQUENCE: 19

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 20
<211> LENGTH: 112
<212> TYPE: PRT
<213> ORGANISM: Artificial sequence
<220> FEATURE:
<223> OTHER INFORMATION: CD3 zeta signaling domain

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 41
<212> TYPE: PRT
<213> ORGANISM: Artificial sequence
<220> FEATURE:
<223> OTHER INFORMATION: CD28 cytoplasmic domain

<400> SEQUENCE: 21

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30
```

```
Pro Arg Asp Phe Ala Ala Tyr Arg Ser
        35                  40
```

<210> SEQ ID NO 22
<211> LENGTH: 42
<212> TYPE: PRT
<213> ORGANISM: Artificial sequence
<220> FEATURE:
<223> OTHER INFORMATION: 4-1BB intracellular TRAF binding domain

<400> SEQUENCE: 22

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 23
<211> LENGTH: 38
<212> TYPE: PRT
<213> ORGANISM: Artificial sequence
<220> FEATURE:
<223> OTHER INFORMATION: ICOS intracellular domain

<400> SEQUENCE: 23

```
Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35
```

<210> SEQ ID NO 24
<211> LENGTH: 42
<212> TYPE: PRT
<213> ORGANISM: Artificial sequence
<220> FEATURE:
<223> OTHER INFORMATION: OX40 intracellular domain

<400> SEQUENCE: 24

```
Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40
```

<210> SEQ ID NO 25
<211> LENGTH: 48
<212> TYPE: PRT
<213> ORGANISM: Artificial sequence
<220> FEATURE:
<223> OTHER INFORMATION: CD27 intracellular domain

<400> SEQUENCE: 25

```
Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 26
<211> LENGTH: 194
<212> TYPE: PRT
<213> ORGANISM: Artificial sequence
<220> FEATURE:
<223> OTHER INFORMATION: CD127 intracellular domain

<400> SEQUENCE: 26

```
Lys Arg Ile Lys Pro Ile Val Trp Pro Ser Leu Pro Asp His Lys Lys
1               5                   10                  15

Thr Leu Glu His Leu Cys Lys Lys Pro Arg Lys Asn Leu Asn Val Ser
            20                  25                  30

Phe Asn Pro Glu Ser Phe Leu Asp Cys Gln Ile His Arg Val Asp Asp
        35                  40                  45

Ile Gln Ala Arg Asp Glu Val Glu Gly Phe Leu Gln Asp Thr Phe Pro
    50                  55                  60

Gln Gln Leu Glu Glu Ser Glu Lys Gln Arg Leu Gly Gly Asp Val Gln
65                  70                  75                  80

Ser Pro Asn Cys Pro Ser Glu Asp Val Val Ile Thr Pro Glu Ser Phe
                85                  90                  95

Gly Arg Asp Ser Ser Leu Thr Cys Leu Ala Gly Asn Val Ser Ala Cys
            100                 105                 110

Asp Ala Pro Ile Leu Ser Ser Ser Arg Ser Leu Asp Cys Arg Glu Ser
        115                 120                 125

Gly Lys Asn Gly Pro His Val Tyr Gln Asp Leu Leu Leu Ser Leu Gly
    130                 135                 140

Thr Thr Asn Ser Thr Leu Pro Pro Pro Phe Ser Leu Gln Ser Gly Ile
145                 150                 155                 160

Leu Thr Leu Asn Pro Val Ala Gln Gly Gln Pro Ile Leu Thr Ser Leu
                165                 170                 175

Gly Ser Asn Gln Glu Glu Ala Tyr Val Thr Met Ser Ser Phe Tyr Gln
            180                 185                 190

Asn Gln
```

<210> SEQ ID NO 27
<211> LENGTH: 416
<212> TYPE: PRT
<213> ORGANISM: Artificial sequence
<220> FEATURE:
<223> OTHER INFORMATION: CASP9 domain

<400> SEQUENCE: 27

```
Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110
```

Pro Glu Ile Arg Lys Pro Glu Val Leu Arg Pro Glu Thr Pro Arg Pro
            115                 120                 125

Val Asp Ile Gly Ser Gly Gly Phe Gly Asp Val Gly Ala Leu Glu Ser
130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
            165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
            195                 200                 205

Ala Lys Lys Met Val Leu Ala Leu Leu Glu Leu Ala Gln Gln Asp His
210                 215                 220

Gly Ala Leu Asp Cys Cys Val Val Ile Leu Ser His Gly Cys Gln
225                 230                 235                 240

Ala Ser His Leu Gln Phe Pro Gly Ala Val Tyr Gly Thr Asp Gly Cys
            245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
            275                 280                 285

Gly Glu Gln Lys Asp His Gly Phe Glu Val Ala Ser Thr Ser Pro Glu
            290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
            325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
            355                 360                 365

Asp Ile Phe Glu Gln Trp Ala His Ser Glu Asp Leu Gln Ser Leu Leu
            370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
            405                 410                 415

<210> SEQ ID NO 28
<211> LENGTH: 278
<212> TYPE: PRT
<213> ORGANISM: Artificial sequence
<220> FEATURE:
<223> OTHER INFORMATION: CASP9 truncated domain

<400> SEQUENCE: 28

Val Gly Ala Leu Glu Ser Leu Arg Gly Asn Ala Asp Leu Ala Tyr Ile
1               5                   10                  15

Leu Ser Met Glu Pro Cys Gly His Cys Leu Ile Ile Asn Asn Val Asn
                20                  25                  30

Phe Cys Arg Glu Ser Gly Leu Arg Thr Arg Thr Gly Ser Asn Ile Asp
            35                  40                  45

Cys Glu Lys Leu Arg Arg Arg Phe Ser Ser Leu His Phe Met Val Glu
        50                  55                  60

Val Lys Gly Asp Leu Thr Ala Lys Met Val Leu Ala Leu Leu Glu
65                  70                  75                  80

Leu Ala Gln Gln Asp His Gly Ala Leu Asp Cys Cys Val Val Ile
            85                  90                  95

Leu Ser His Gly Cys Gln Ala Ser His Leu Gln Phe Pro Gly Ala Val
            100                 105                 110

Tyr Gly Thr Asp Gly Cys Pro Val Ser Val Glu Lys Ile Val Asn Ile
            115                 120                 125

Phe Asn Gly Thr Ser Cys Pro Ser Leu Gly Gly Lys Pro Lys Leu Phe
130                 135                 140

Phe Ile Gln Ala Cys Gly Gly Glu Gln Lys Asp His Gly Phe Glu Val
145                 150                 155                 160

Ala Ser Thr Ser Pro Glu Asp Glu Ser Pro Gly Ser Asn Pro Glu Pro
            165                 170                 175

Asp Ala Thr Pro Phe Gln Glu Gly Leu Arg Thr Phe Asp Gln Leu Asp
            180                 185                 190

Ala Ile Ser Ser Leu Pro Thr Pro Ser Asp Ile Phe Val Ser Tyr Ser
            195                 200                 205

Thr Phe Pro Gly Phe Val Ser Trp Arg Asp Pro Lys Ser Gly Ser Trp
            210                 215                 220

Tyr Val Glu Thr Leu Asp Asp Ile Phe Glu Gln Trp Ala His Ser Glu
225                 230                 235                 240

Asp Leu Gln Ser Leu Leu Arg Val Ala Asn Ala Val Ser Val Lys
            245                 250                 255

Gly Ile Tyr Lys Gln Met Pro Gly Cys Phe Asn Phe Leu Arg Lys Lys
            260                 265                 270

Leu Phe Phe Lys Thr Ser
            275

<210> SEQ ID NO 29
<211> LENGTH: 108
<212> TYPE: PRT
<213> ORGANISM: Artificial sequence
<220> FEATURE:
<223> OTHER INFORMATION: FKBP f36v domain

<400> SEQUENCE: 29

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
            35                  40                  45

Phe Met Leu Gly Lys Gln Glu Val Ile Arg Gly Trp Glu Glu Gly Val
        50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
            85                  90                  95

Thr Leu Val Phe Asp Val Glu Leu Leu Lys Leu Glu
            100                 105

<210> SEQ ID NO 30
<211> LENGTH: 22
<212> TYPE: PRT
<213> ORGANISM: Artificial sequence

```
<220> FEATURE:
<223> OTHER INFORMATION: 2A peptide linker

<400> SEQUENCE: 30

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 31
<211> LENGTH: 20
<212> TYPE: PRT
<213> ORGANISM: Artificial sequence
<220> FEATURE:
<223> OTHER INFORMATION: 2A peptide linker

<400> SEQUENCE: 31

Gln Cys Thr Asn Tyr Ala Leu Leu Lys Leu Ala Gly Asp Val Glu Ser
1               5                   10                  15

Asn Pro Gly Pro
            20

<210> SEQ ID NO 32
<211> LENGTH: 18
<212> TYPE: PRT
<213> ORGANISM: Artificial sequence
<220> FEATURE:
<223> OTHER INFORMATION: 2A peptide linker

<400> SEQUENCE: 32

Glu Gly Arg Gly Ser Leu Leu Thr Cys Gly Asp Val Glu Glu Asn Pro
1               5                   10                  15

Gly Pro

<210> SEQ ID NO 33
<211> LENGTH: 19
<212> TYPE: PRT
<213> ORGANISM: Artificial sequence
<220> FEATURE:
<223> OTHER INFORMATION: 2A peptide linker

<400> SEQUENCE: 33

Ala Thr Asn Phe Ser Leu Leu Lys Gln Ala Gly Asp Val Glu Glu Asn
1               5                   10                  15

Pro Gly Pro

<210> SEQ ID NO 34
<211> LENGTH: 242
<212> TYPE: PRT
<213> ORGANISM: Artificial sequence
<220> FEATURE:
<223> OTHER INFORMATION: CD19 scfv

<400> SEQUENCE: 34

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60
```

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
            165                 170                 175

Glu Thr Thr Tyr Tyr Ser Ser Leu Lys Ser Arg Val Thr Ile Ser
            180                 185                 190

Lys Asp Asn Ser Lys Asn Gln Val Ser Leu Lys Leu Ser Ser Val Thr
    195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 35
<211> LENGTH: 242
<212> TYPE: PRT
<213> ORGANISM: Artificial sequence
<220> FEATURE:
<223> OTHER INFORMATION: CD19 scfv

<400> SEQUENCE: 35

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
            165                 170                 175

Glu Thr Thr Tyr Tyr Gln Ser Ser Leu Lys Ser Arg Val Thr Ile Ser

```
                 180                 185                 190
Lys Asp Asn Lys Asn Gln Val Ser Leu Lys Leu Ser Ser Val Thr
            195                 200                 205

Ala Ala Asp Thr Ala Val Tyr Tyr Cys Ala Lys His Tyr Tyr Gly
 210                 215                 220

Gly Ser Tyr Ala Met Asp Tyr Trp Gly Gln Gly Thr Leu Val Thr Val
225                 230                 235                 240

Ser Ser

<210> SEQ ID NO 36
<211> LENGTH: 242
<212> TYPE: PRT
<213> ORGANISM: Artificial sequence
<220> FEATURE:
<223> OTHER INFORMATION: CD19 scFV

<400> SEQUENCE: 36

Gln Val Gln Leu Gln Glu Ser Gly Pro Gly Leu Val Lys Pro Ser Glu
 1               5                  10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 37
<211> LENGTH: 242
<212> TYPE: PRT
<213> ORGANISM: Artificial sequence
<220> FEATURE:
<223> OTHER INFORMATION: CD19 scfv

<400> SEQUENCE: 37
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 38
<211> LENGTH: 247
<212> TYPE: PRT
<213> ORGANISM: Artificial sequence
<220> FEATURE:
<223> OTHER INFORMATION: CD19 scfv

<400> SEQUENCE: 38

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Ser Gly Gly Gly Ser Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Leu Lys Ser
                180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 39
<211> LENGTH: 247
<212> TYPE: PRT
<213> ORGANISM: Artificial sequence
<220> FEATURE:
<223> OTHER INFORMATION: CD19 scfv

<400> SEQUENCE: 39

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
                180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 40
<211> LENGTH: 247
<212> TYPE: PRT
<213> ORGANISM: Artificial sequence
<220> FEATURE:
<223> OTHER INFORMATION: CD19 scfv

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 41
<211> LENGTH: 247
<212> TYPE: PRT
<213> ORGANISM: Artificial sequence
<220> FEATURE:
<223> OTHER INFORMATION: CD19 scfv

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Gly Lys Gly Leu Glu Trp Ile
            35                  40                  45

Gly Val Ile Trp Gly Ser Glu Thr Thr Tyr Tyr Gln Ser Ser Leu Lys
50                      55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Glu Ile Val Met
        130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 42
<211> LENGTH: 247
<212> TYPE: PRT
<213> ORGANISM: Artificial sequence
<220> FEATURE:
<223> OTHER INFORMATION: CD19 scfv

<400> SEQUENCE: 42

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 43
<211> LENGTH: 247
<212> TYPE: PRT
<213> ORGANISM: Artificial sequence
<220> FEATURE:
<223> OTHER INFORMATION: CD19 scfv

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 44
<211> LENGTH: 242
<212> TYPE: PRT
<213> ORGANISM: Artificial sequence
<220> FEATURE:
<223> OTHER INFORMATION: CD19 scfv

<400> SEQUENCE: 44

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
            115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 45
<211> LENGTH: 242
<212> TYPE: PRT
<213> ORGANISM: Artificial sequence
<220> FEATURE:
<223> OTHER INFORMATION: CD19 scfv

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

```
Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys
```

CAR BASED IMMUNOTHERAPY

CROSS-REFERENCE TO RELATED APPLICATIONS

This application is a national stage filing under 35 U.S.C. § 371 of international application PCT/US2015/032245, entitled "CAR BASED IMMUNOTHERAPY", filed May 22, 2015, which was published under PCT Article 21(2) in English and which claims the benefit under 35 U.S.C. § 119(e) of U.S. provisional application No. 62/002,603, entitled "CAR-BASED IMMUNOTHERAPY", filed May 23, 2014, the entire teachings of each of which are herein incorporated by reference.

BACKGROUND

The chimeric antigen receptor (CAR) provides a promising approach for adoptive T-cell immunotherapy for cancer. Commonly, CARs comprise a single chain fragment variable (scFv) region of an antibody or a binding domain specific for a tumor associated antigen (TAA) coupled via hinge and transmembrane regions to cytoplasmic domains of T-cell signaling molecules. The most common lymphocyte activation moieties include a T-cell costimulatory domain in tandem with a T-cell effector function triggering (e.g. CD3ξ) moiety. The CAR-mediated adoptive immunotherapy allows CAR-grafted T cells to directly recognize the TAAs on target tumor cells in a non-HLA-restricted manner.

The large majority of patients having B-cell malignancies, including B cell acute lymphocytic leukemia (B-ALL) and chronic lymphocytic leukemia (CLL), will die from their disease. One approach to treating these patients is to genetically modify T cells to target antigens expressed on tumor cells through the expression of CARs. CARs are antigen receptors that are designed to recognize cell surface antigens in a human leukocyte antigen (HLA)-independent manner. Attempts in using genetically modified cells expressing CARs to treat these types of patients have met with promising success.

In most cancers, tumor-specific antigens are not yet well defined, but in B cell malignancies, CD19 is an attractive tumor target. Expression of CD19 is restricted to normal and malignant B cells (Uckun, et al. Blood, 1988, 71: 13-29), so that CD19 is a widely accepted target to safely test CARs,

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

The invention relates in part to compositions and methods for treating cancer including, but not limited to, blood types of cancer. The present invention relates to a strategy of adoptive cell transfer of T cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

The present invention, in some embodiments, provides for a compositions where a CAR, or portions thereof, is fully human, thereby minimizing the risk for a host immune response.

The present invention, in some embodiments, relates generally to the use of T cells genetically modified to stably express a desired CAR. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcR protein into a single chimeric protein. In a specific example the CAR an antigen binding domain, a transmembrane domain, a costimulatory signaling region, and a CD3 zeta signaling domain, wherein the costimulatory signaling region comprises a CD28 signaling domain, a CD137 signaling domain and a CD27 signaling domain, along with a self-destructive gene design such as induced caspase 9 (iCasp9) gene. In an even more specific embodiment, the arrangement of the elements of the CAR is as follows:

scFv-28-137-27-CD3z-2A-iCasp9

The CD28 element may, but not necessarily, comprise at least a portion of the transmembrane domain of the CAR embodiment above. The CAR may also include several hinge elements and/or spacer sequences (such as between individual domain elements).

Figure 1:
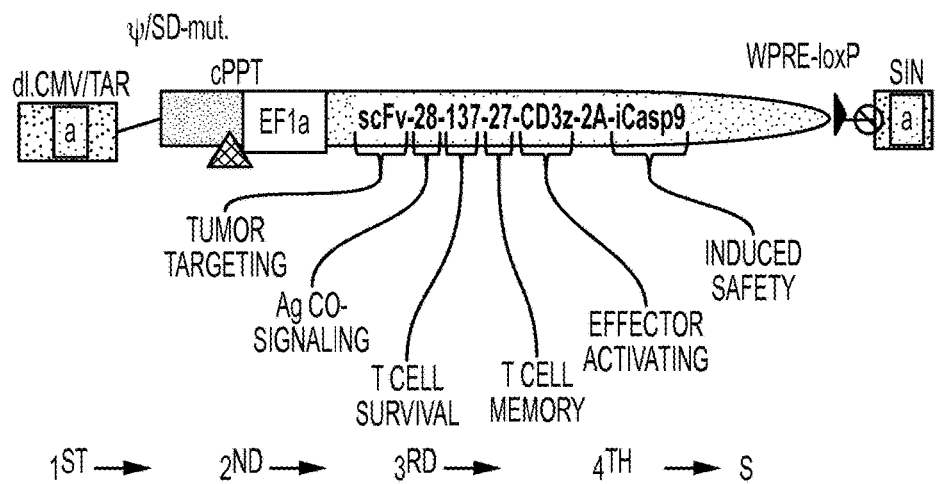
FIG. 1 provides a schematic of a CAR-4S lentiviral design.

Embodiments of the present invention relate to a CAR that incorporates a novel series of domains that provide different functional aspects that synergistically work together to improve efficacy. For example, the CAR includes, in some embodiments, an antigen recognition domain, an antigen co-signaling domain that stimulates activity, a survival domain that increases T-cell survival, T-cell memory domain, and an effector activating domain. Alternatively, the CAR may further include a domain that induces safety. FIG. 1 provides an example of a series of domains that achieve this multi-functionality.

In some embodiments, the CAR of the invention comprises an extracellular domain having an antigen recognition domain, a transmembrane domain, and a multi-functional cytoplasmic domain. In some embodiments, two CAR proteins dimerize (e.g., form homo- or heterodimers) in vivo. In some embodiments, the CAR can comprise a fully human antibody or antibody fragment, e.g., a scFv. In one embodiment, the transmembrane domain that naturally is associated with one of the domains in the CAR is used. In some embodiments, the transmembrane domain can be selected or modified by amino acid substitution to avoid binding of such domains to the transmembrane domains of the same or different surface membrane proteins to minimize interactions with other members of the receptor complex. In some embodiments, the transmembrane domain is a CD8a transmembrane domain.

In some embodiments, the CAR T cells of the invention can be generated by introducing a lentiviral vector comprising a nucleic acid encoding a desired CAR targeting a tumor antigen into the cells. For example, the lentiviral vector comprises a nucleic acid encoding CAR comprising a tumor antigen binding domain (e.g., targets CD19), optionally a CD8a hinge, a transmembrane domain, and CD28, CD137, CD27 and CD3-zeta signaling domains, into the cells. In some embodiments, the CAR T cells of the invention are able to replicate in vivo resulting in long-term persistence that can lead to sustained tumor control. In some embodiments, the CAR T cells of the invention can be generated by transfecting an RNA encoding the desired CAR, into the cells. In some embodiments, the CAR is transiently expressed in the genetically modified CAR T cells.

In some embodiments, the invention relates to a CAR comprising a human antibody, or fragments thereof. The invention is based, in part, upon the discovery that a CAR comprising an antigen recognition domain comprising a fully human antibody fragment specifically recognizes tumor antigens. Therefore, in some embodiments, human CARs of the invention can be used to treat cancers and other disorders and avoid the risk of inducing an immune response.

In some embodiments, the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

The invention may include using T cells expressing a CAR comprising an antigen binding domain, a transmembrane domain, a costimulatory signaling region, and a CD3 zeta signaling domain, wherein the costimulatory signaling region comprises a CD28 signaling domain, a CD137 signaling domain and a CD27 signaling domain. In some embodiments, CAR T cells of the invention can undergo robust in vivo T cell expansion and can establish specific memory cells that persist at high levels for an extended amount of time in blood and bone marrow. In some instances, the CAR T cells of the invention infused into a patient can eliminate cancerous cells in vivo in patients with cancer.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20% or +10%, more preferably +5%, even more preferably +1%, and still more preferably +0.1% from the specified value, as such variations are appropriate to perform the disclosed methods.

As used herein, the terms "FRa binding domain" may refer to any FRa specific binding domain, known to one of skilled in the art. In one example, FRa binding domain comprises a single-chain variable fragment (scFv) comprising the variable regions of the heavy ($V_H$) and light chains ($V_L$) of an antibody binding specifically to FRa. Anti-FRa antibodies, antibody fragments, and their variants are well known in the art and fully described in U.S. Patent Publications U.S 20100055034; U.S. 20090324594; U.S. 20090274697; U.S. 20080260812; U.S. 20060239910; U.S. 20050232919; U.S. 20040235108, all of which are incorporated by reference herein in their entirety. In one embodiment, the FRa binding domain is a homologue, a variant, an isomer, or a functional fragment of an anti-FRa antibody. Each possibility represents a separate embodiment of the present invention.

In some embodiments, a "protein domain" or "domain" refers to a distinct globular unit that can be identified as such by a structure determination method such as X-ray crystallography or NMR, by other biophysical methods such as scanning calorimetry according to which a protein domain melts as a distinct unit (see for example Pabo et al. Proc Natl Acad Sci USA. (1979) 76(4):1608-12), or by sequence similarity to protein domains whose structure has been determined. The SCOP database (Murzin et al. J Mol Biol. (1995) 247(4):536-40) provides the identification of protein domains so that the domain organization of a new protein can be identified by sequence comparison. Protein domains may comprise an amino acid sequence that is sufficient to drive folding of such a polypeptide into a discrete structure, in which essentially all of the rotatable bonds along the main chain of the polypeptide are constrained to within about 10 degrees.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies, human antibodies, and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, single chain antibodies (e.g., scFv antibodies), and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "tumor antigen" as used herein refers to an antigen associated with a cancer cell. Examples of tumor antigens include but are not limited to CD19, CD20, CD22, ROR1, mesothelin, CD33/IL3Ra, c-Met, PSMA, Glycolipid F77, EGFRvIII, GD-2, NY-ESO-1 TCR, and MAGE A3 TCR.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species. "Xenogeneic" refers to a graft derived from an animal of a different species.

The term "cancer" as used herein is defined as a disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In a specific embodiment, cancer refers to B-cell related malignancies.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor. A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lenti viruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lenti viruses. Vectors derived from lenti viruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Codon-optimized" means that codons relating to a specific amino acid are optimized for translational efficiency of a gene of interest. Codon optimization typically involves evaluating the gene or sequence of interest and substituting the codon with a more prevalent or common codon used for the same amino acid in a specific cell or species. Programs used by those in the art to evaluate codon optimization include those provided by Integrated DNA Technologies, EnCor Biotechnology, Inc., JCat, OptimumGene™ (GenScript USA, Inc., Pisataway, N.J. 08854), etc. The sequences encoding the CAR embodiments described herein may be codon-optimized, which can increase their translational efficiency.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides, in some embodiments, compositions and methods for treating cancer among other diseases. The cancer may be a hematological malignancy, a solid tumor, a primary or a metastasizing tumor. Alternatively, embodiments of the disclosure may be used to treat other diseases, including infectious diseases.

In some embodiments, the invention provides a cell (e.g., T cell) engineered to express a CAR wherein the CAR T cell exhibits an antitumor property. In a preferred embodiment, the CAR is a fully human CAR. The CAR of the invention can be engineered to comprise an extracellular domain having an antigen binding domain fused to an intracellular signaling domain of the T cell antigen receptor complex zeta chain (e.g., CD3 zeta). The CAR of the invention when expressed in a T cell is, in some embodiments, able to redirect antigen recognition based on the antigen binding specificity. An exemplary antigen is CD19 because this antigen is expressed on malignant B-cells. However, the invention is not limited to targeting CD19. Rather, the invention includes any antigen binding moiety that when bound to its cognate antigen, affects a tumor cell so that the tumor cell fails to grow, is prompted to die, or otherwise is affected so that the tumor burden in a patient is diminished or eliminated. The antigen binding moiety is, in some embodiments, fused with an intracellular domain from multiple costimulatory molecules and a zeta chain.

In some embodiments, the CAR of the invention comprises an arrangement as follows:
scFv-28-137-27-CD3z-2A-iCasp9

In some embodiments, the above exemplary, non-limiting arrangement is from left to right, the N-terminus to C-terminus of the CAR. The CAR may comprise or further comprise any other combination of elements as described herein.

Composition

The present invention, in some embodiments, provides a chimeric antigen receptor (CAR) comprising an extracellular and intracellular domain. In some embodiments, the CAR of the invention is fully human. The extracellular domain comprises, in some embodiments, a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

It is to be understood that a CAR can include a region (e.g., an antigen binding domain, a transmembrane domain, a cytoplasmic domain, a signaling domain, a safety domain and/or a linker, or any combination thereof) having a sequence provided herein or a variant thereof or a fragment of either one thereof (e.g., a variant and/or fragment that retains the function required for the CAR activity) can be included in a CAR protein as described herein. In some embodiments, a variant has 1, 2, 3, 4, 5, 6, 7, 8, 9, or 10 amino acid changes relative to the illustrated sequence. In some embodiments, a variant has a sequence that is at least 80%, at least 85%, at least 90%, 90%-95%, at least 95% or at least 99% identical to the illustrated sequence. In some embodiments, a fragment is 1-5, 5-10, 10-20, 20-30, 30-40, or 40-50 amino acids shorter than a sequence provided herein. In some embodiments, a fragment is shorter at the N-terminal, C-terminal, or both terminal regions of the sequence provided. In some embodiments, a fragment contains 80%-85%, 85%-90%, 90%-95%, or 95%-99% of the number of amino acids in a sequence provided herein.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

In some embodiments, the spacer and/or hinge sequences of the CAR are selected from one or more of the following spacer sequences or hinge sequences:

Spacer Sequences:
(SEQ ID NO: 1)
GGGGS (SEQ ID NO: 2)
GGGGSGGGGS (SEQ ID NO: 3)
GGGGS x3

G518:
(SEQ ID NO: 4)
GSTSGGGSGGGSGGGSS

218S:
(SEQ ID NO: 5)
GSTSGSGKPGSSEGSTKG

G58:
(SEQ ID NO: 6)
GGGGSGGG

Hinge Sequences:
Native:
(SEQ ID NO: 7)
VEPKSCDKTHTCPPCP

C2335:
(SEQ ID NO: 8)
LDPKSSDKTHTCPPCP

C233P:
(SEQ ID NO: 9)
VEPKSPDKTHTCPPCP

DeLta5:
(SEQ ID NO: 10)
LDKTHTCPPCP

Antigen Binding Moiety

In some embodiments, the CAR of the invention comprises a target-specific binding element otherwise referred to as an antigen binding moiety or antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells. In some embodiments, the CAR of the invention can be engineered to target a tumor antigen of interest by way of engineering a desired antigen binding moiety that specifically binds to an antigen on a tumor cell. In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

The antigen binding domain of the CAR may target, for example, CD19, CD20, CD22, ROR1, mesothelin, CD33/ IL3Ra, c-Met, CD37 PSMA, Glycolipid F77, HER2, EGFRvIII, GD-2, NY-ESO-1 TCR, and MAGE A3 TCR. Alternatively, the antigen binding domain portion of the CAR targets an antigen that includes but is not limited to FRalpha, CD24, CD44, CD133, CD166, epCAM, CA-125, HE4, Oval, estrogen receptor, progesterone receptor, HER-2/neu, uPA, PAI-1, and the like. Other antigens specific for cancer that may be targeted at taught in PCT publication No. WO2013/123061 (page 20).

The antigen binding domain can be any domain that binds to the antigen including but not limited to monoclonal antibodies, single chain antibodies (e.g., scFvs), polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or fragment thereof. Thus, in one embodiment, the antigen biding domain portion comprises a human antibody or a fragment thereof.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO91/10741; each of which is incorporated herein by reference in its entirety. A human antibody can also be an antibody wherein the heavy and light chains are encoded by a nucleotide sequence derived from one or more sources of human DNA. Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Antibodies directed against an antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For a detailed discussion of this technology for producing human antibodies and human monoclonal antibodies and protocols for producing such antibodies, see, e.g., PCT Publication Nos. WO2014/ 055771, WO 98/24893, WO 96/34096, and WO 96/33735; and U.S. Pat. Nos. 5,413,923; 5,625,126; 5,633,425; 5,569, 825; 5,661,016; 5,545,806; 5,814,318; and 5,939,598, each of which is incorporated by reference herein in their entirety.

A "humanized" antibody retains a similar antigenic specificity as the original antibody, i.e., in the present invention, the ability to bind, for example, CD19.

In some embodiments, the antigen binding moiety portion of the CAR of the invention targets CD19. Preferably, in some embodiments, the antigen binding moiety portion in the CAR of the invention is a fully human anti-CD19 scFV. Exemplary CD19 scFVs are taught in U.S. Pat. Nos. 7,902, 338 and 7,109,304, and in U.S. Published Application Numbers US20070178103 and US20130287748, and in PCT Published Application Number WO2014153270A1, each of which are incorporated herein by reference with respect to the teachings related to CD19 scFVs. Exemplary CD19 scFVs are provided in the sequences of SEQ ID NOs: 34-45. In some embodiments, the CD19 scFV comprises the sequence of any one of SEQ ID NOs: 34-45 or a variant thereof that is at least 80%, 85%, 90%, 95%, 98% or 99% identical to any one of SEQ ID NOs: 34-45.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (e.g., comprise at least the transmembrane region(s) of) the alpha, beta or zeta chain of the T-cell receptor, CD28, CD3 epsilon, CD45, CD4, CD5, CD8, CD9, CD16, CD22, CD27, CD33, CD37, CD64, CD80, CD86, CD134, CD137, and CD154. In some instances, a variety of human hinges can be employed as well including the human Ig (immunoglobulin) hinge. Transmembrane domains can be identified using any method known in the art or described herein, e.g., by using the UniProt Database.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In some embodiments, the transmembrane domain in the CAR of the invention is the CD8 transmembrane domain. Sequences of CD8 for this purposes are taught in PCT pub no. WO2014/055771.

In some embodiments, the transmembrane domain in the CAR of the invention is the CD28 transmembrane domain.

In some embodiments, the transmembrane domain in the CAR of the disclosure is a CD28 transmembrane domain. An exemplary sequence of CD28 is provided below, as well as an exemplary transmembrane domain sequence. In some embodiments, the CD28 transmembrane domain comprises the exemplary transmembrane domain sequence below, or a fragment or variant thereof that is capable of anchoring a CAR comprising the sequence to a cell membrane. One skilled in the art would appreciate that the full transmembrane domain, or portion thereof, may be implemented with the cytoplasmic domain, or a portion thereof. In some embodiments, the transmembrane and cytoplasmic domains used would be contiguous portions of the CD28 sequence.

CD28 (amino acids 19-220)
(SEQ ID NO: 11)
NKILVKQSPMLVAYDNAVNLSCKYSYNLFSREFRASLHKGLDSAVEVCVV

YGNYSQQLQVYSKTGFNCDGKLGNESVTFYLQNLYVNQTDIYFCKIEVMY

PPPYLDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAAY

RS

CD28 (amino acids 153-179, transmembrane domain)
(SEQ ID NO: 12)
FWVLVVVGGVLACYSLLVTVAFIIFWV In some embodiments, the CAR of the disclosure is comprises a region of CD28 that contains all or part of an extracellular domain, all or part of a transmembrane domain and all or part of a cytoplasmic domain. An exemplary sequence of a region of CD28 for inclusion in a CAR is provided below. In some embodiments, the CD28 transmembrane domain comprises the exemplary transmembrane domain sequence below, or a fragment or variant thereof that is capable of anchoring a CAR comprising the sequence to a cell membrane.

CD28 region
(SEQ ID NO: 13)
IEVMYPPPYLDNEKSNGTIIHVKGKHLCPSPLFPGPSKPFWVLVVVGGVL
ACYSLLVTVAFIIFWVRSKRSRLLHSDYMNMTPRRPGPTRKHYQPYAPPR
DFAAYRSAS In some embodiments, the transmembrane domain in the CAR of the disclosure is a CD27 transmembrane domain. An exemplary sequence of CD27 is provided below. One skilled in the art would appreciate that the full transmembrane domain of CD27, or portion thereof, may be implemented with the cytoplasmic domain, or a portion thereof. In some embodiments, the domains would be contiguous portions of the CD27 sequence.

CD27 (amino acids 20-260)
(SEQ ID NO: 14)
ATPAPKSCPERHYWAQGKLCCQMCEPGTFLVKDCDQHRKAAQCDPCIPGV

SFSPDHHTRPHCESCRHCNSGLLVRNCTITANAECACRNGWQCRDKECTE

CDPLPNPSLTARSSQALSPHPQPTHLPYVSEMLEARTAGHMQTLADFRQL

PARTLSTHWPPQRSLCSSDFIRILVIFSGMFLVFTLAGALFLHQRRKYRS

NKGESPVEPAEPCHYSCPREEEGSTIPIQEDYRKPEPACSP

In some embodiments, the transmembrane domain of the CAR of the disclosure comprises a hinge domain such as a CD8 hinge domain. See PCT pub No. WO2014/055771, which teaches an exemplary CD8 hinge domain sequence. An exemplary CD8 hinge domain sequence is also provided below. In some embodiments, the CD8 hinge domain comprises the exemplary sequence below, or a fragment or variant thereof that is capable of providing flexibility to or preventing steric hindrance of the CAR or the domain(s) attached to the hinge domain. In some instances, a variety of human hinges can be employed as well including the human Ig (immunoglobulin) hinge.

CD8 hinge domain
(SEQ ID NO: 15)
AKPTTTPAPRPPTPAPTIASQPLSLRPEACRPAAGGAVHTRGLDFACD Cytoplasmic Domain In some embodiments, the cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

The cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. Thus, while the invention in exemplified primarily with CD28, CD137 and CD27 as the co-stimulatory signaling element, other additional costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In some embodiments, the cytoplasmic domain is designed to comprise the signaling domain of CD3-zeta and the signaling domain of CD28, CD137 and CD27.

In some embodiments, the cytoplasmic domain comprises a CD27 intracellular signaling domain (e.g., CD27 cytoplasmic signaling domain). In some embodiments, the CD27 signaling domain displays effector signaling function that enhances immune effector activities including, but not limited to cell proliferation and cytokine production. An exemplary CD27 signaling domain sequence is provided below. In some embodiments, the CD27 signaling domain comprises the exemplary sequence below, or a fragment or variant thereof that, when included in a CAR, has the same or an improved function (such as cytolytic activity, cell proliferation or secretion of cytokines) compared to a CAR comprising the exemplary sequence below. The function may be tested using any suitable method known in the art.

```
CD27 signaling domain
                                          (SEQ ID NO: 16)
QRRKYRSNKGESPVEPAEPCHYSCPREEEGSTIPIQEDYRKPEPACSP
```

In some embodiments, the cytoplasmic domain comprises a CD137 intracellular signaling domain (e.g., CD137 cytoplasmic signaling domain). An exemplary CD137 signaling domain sequence is provided below.

```
    CD137 signaling domain
                                          (SEQ ID NO: 17)
    KRGRKKLLYIFKQPFMRPVQTTQEEDGCSCRFPEEEEGGCEL
```

In some embodiments, the cytoplasmic domain comprises a CD28 intracellular signaling domain (e.g., CD28 cytoplasmic signaling domain). An exemplary CD28 signaling domain sequence is provided below.

```
    CD28 signaling domain
                                          (SEQ ID NO: 18)
    RSKRSRLLHSDYMNMTPRRPGPTRKHYQPYAPPRDFAAYRS
```

In some embodiments, the CAR of the disclosure comprises a cytoplasmic signaling sequence derived from CD3zeta. Examples of CD3 zeta domain sequences are provided below. In some embodiments, the CD3zeta signaling domain comprises one of the CD3 zeta sequences below, or a fragment or variant thereof that, when included in a CAR, has the same or an improved function (such as cytolytic activity or secretion of cytokines) compared to a CAR comprising the sequence below.

```
CD3 zeta signaling domain
                                          (SEQ ID NO: 19)
RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR CD3 zeta signaling domain
                                          (SEQ ID NO: 20)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR
```

The cytoplasmic domain of the CAR can be designed to comprise a CD3-zeta signaling domain combined with any other desired cytoplasmic domain(s) useful in the context of the CAR of the disclosure. For example, the cytoplasmic domain of the CAR can comprise a CD3 zeta domain and a costimulatory signaling region. The costimulatory signaling region refers to a portion of the CAR comprising the intracellular domain of a costimulatory molecule. Thus, while the disclosure is exemplified primarily with 4-1BB, CD28, CD137 and CD27 as the co-stimulatory signaling element, other additional costimulatory elements are within the scope of the disclosure. Example sequences of co-stimulatory signaling regions are shown below.

```
CD28 (amino acids 180-220, cytoplasmic domain)
                                          (SEQ ID NO: 21)
RSKRSRLLHSDYMNMTPRRPGPTRKHYQPYAPPRDFAAYRS 4-1BB (CD137) intracellular TRAF binding domain
                                          (SEQ ID NO: 22)
KRGRKKLLYIFKQPFMRPVQTTQEEDGCSCRFPEEEEGGCEL ICOS intracellular domain
                                          (SEQ ID NO: 23)
CWLTKKKYSSSVHDPNGEYMFMRAVNTAKKSRLTDVTL OX40 intracellular domain
                                          (SEQ ID NO: 24)
ALYLLRRDQRLPPDAHKPPGGGSFRTPIQEEQADAHSTLAKI CD27 intracellular domain
                                          (SEQ ID NO: 25)
QRRKYRSNKGESPVEPAEPCHYSCPREEEGSTIPIQEDYRKPEPACSP CD127 intracellular domain
                                          (SEQ ID NO: 26)
KRIKPIVWPSLPDHKKTLEHLCKKPRKNLNVSFNPESFLDCQIHRVDDIQ
ARDEVEGFLQDTFPQQLEESEKQRLGGDVQSPNCPSEDVVITPESFGRDS
SLTCLAGNVSACDAPILSSSRSLDCRESGKNGPHVYQDLLLSLGTTNSTL
PPPFSLQSGILTLNPVAQGQPILTSLGSNQEEAYVTMSSFYQNQ
```

In some embodiments, CAR of the disclosure comprises the apoptosis inducing gene Casp9 or a domain or truncated version thereof. An exemplary Casp9 sequence and truncated sequence is below. In some embodiments, the CAR comprises a linker (e.g., a peptide linker) between a CD3 zeta domain and Casp9.

In some embodiments, CAR of the disclosure comprises the apoptosis inducing gene Casp9 or a domain or truncated version thereof. An exemplary Casp9 sequence and truncated sequence is below. In some embodiments, the CAR comprises a linker (e.g., a peptide linker) between a CD3 zeta domain and Casp9.

CASP9 amino acid sequence
(SEQ ID NO: 27)
MDEADRRLLRRCRLRLVEELQVDQLWDALLSRELFRPHMIEDIQRAGSGS
RRDQARQLIIDLETRGSQALPLFISCLEDTGQDMLASFLRTNRQAAKLSK
PTLENLTPVVLRPEIRKPEVLRPETPRPVDIGSGGFGDVGALESLRGNAD
LAYILSMEPCGHCLIINNVNFCRESGLRTRTGSNIDCEKLRRRFSSLHFM
VEVKGDLTAKKMVLALLELAQQDHGALDCCVVVILSHGCQASHLQFPGAV
YGTDGCPVSVEKIVNIFNGTSCPSLGGKPKLFFIQACGGEQKDHGFEVAS
TSPEDESPGSNPEPDATPFQEGLRTFDQLDAISSLPTPSDIFVSYSTFPG
FVSWRDPKSGSWYVETLDDIFEQWAHSEDLQSLLLRVANAVSVKGIYKQ
MPGCFNFLRKKLFFKTS A truncated CASP9 amino acid sequence
(SEQ ID NO: 28)
VGALESLRGNADLAYILSMEPCGHCLIINNVNFCRESGLRTRTGSNIDCE
KLRRRFSSLHFMVEVKGDLTAKKMVLALLELAQQDHGALDCCVVVILSHG
CQASHLQFPGAVYGTDGCPVSVEKIVNIFNGTSCPSLGGKPKLFFIQACG
GEQKDHGFEVASTSPEDESPGSNPEPDATPFQEGLRTFDQLDAISSLPTP
SDIFVSYSTFPGFVSWRDPKSGSWYVETLDDIFEQWAHSEDLQSLLLRVA
NAVSVKGIYKQMPGCFNFLRKKLFFKTS In some embodiments, the peptide linker between the CD3 zeta domain and the Casp9 domain is a 2A peptide linker. A "2A peptide linker" refers to an amino acid sequence encoding the 2A region of a picornavirus (e.g., foot-and-mouth disease virus (F2A), equine rhinitis A virus (E2A), Thosea asigna virus (T2A), and porcine teschovirus-1 (P2A)), or a portion thereof. Generally, 2A peptide linkers enable multicistronic protein expression by causing ribosome skipping. Examples of 2A linkers are provided below.

F2A:
(SEQ ID NO: 30)
VKQTLNFDLLKLAGDVESNPGP

E2A:
(SEQ ID NO: 31)
QCTNYALLKLAGDVESNPGP

T2A:
(SEQ ID NO: 32)
EGRGSLLTCGDVEENPGP

P2A:
(SEQ ID NO: 33)
ATNFSLLKQAGDVEENPGP

In some embodiments, the cytoplasmic domain further comprises an iCasp9 domain and/or a FKBP domain. Generally, FK506 binding proteins (FKBP) dimerize in the presence of certain small molecules (e.g., FK1012, FK506, FKCsA, rapamycin, coumermycin, gibberellin, HaXS, etc.). Thus, FKBP are useful for performing chemical dimerization. For example, an FKBP domain may be fused to inactive caspase 9 (iCasp9). In the presence of certain small molecules, the iCasp9-FKBP protein will dimerize and activate Casp9, thereby inducing apoptosis of the cell containing the iCasp9-FKBP fusion protein. An exemplary mutated FK506 binding protein motif is provided below.

FKBP f36v amino acid sequence
(SEQ ID NO: 29)
MGVQVETISPGDGRTFPKRGQTCVVHYTGMLEDGKKVDSSRDRNKPFKF
MLGKQEVIRGWEEGVAQMSVGQRAKLTISPDYAYGATGHPGIIPPHATL
VFDVELLKLE In some embodiments, a CAR comprises or consists of the sequence below, which is broken down by exemplary domains included therein:

Anti-CD19 scFv chain 1 (e.g., a chain 1 of any one of SEQ ID NOs: 34-45)
GSTSGSGKPGSSEGSTKG (optional linker; SEQ ID NO: 5)

Anti-CD19 scFV chain 2 (e.g., a chain 2 of any one of SEQ ID NOs: 34-45)
GSTSGSGKPGSSEGSTKG (optional linker; SEQ ID NO: 5)

FWVLVVVGGVLACYSLLVTVAFIIFWV (CD28 transmembrane domain; SEQ ID NO: 12)

KRGRKKLLYIFKQPFMRPVQTTQEEDGCSCRFPEEEEGGCEL (CD137 cytoplasmic signaling domain; SEQ ID NO: 17)

GSTSGSGKPGSSEGSTKG (optional linker; SEQ ID NO: 5)

QRRKYRSNKGESPVEPAEPCHYSCPREEEGSTIPIQEDYRKPEPACSP (CD27 cytoplasmic signaling domain; SEQ ID NO: 14)

RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR (CD3 zeta signaling domain; SEQ ID NO: 19)

2A Linker (e.g., any one of SEQ ID NOs. 30-33)
VGALESLRGNADLAYILSMEPCGHCLIINNVNFCRESGLRTRTGSNIDCE
KLRRRFSSLHFMVEVKGDLTAKKMVLALLELAQQDHGALDCCVVVILSHG
CQASHLQFPGAVYGTDGCPVSVEKIVNIFNGTSCPSLGGKPKLFFIQACG
GEQKDHGFEVASTSPEDESPGSNPEPDATPFQEGLRTFDQLDAISSLPTP
SDIFVSYSTFPGFVSWRDPKSGSWYVETLDDIFEQWAHSEDLQSLLLRVA
NAVSVKGIYKQMPGCFNFLRKKLFFKTS
(truncated Casp9, SEQ ID NO: 28).

However, it should be appreciated that other combinations of sequences described herein can be used in a CAR.

Vectors

In some embodiments, the present invention encompasses a DNA construct comprising sequences of a CAR, wherein the sequence comprises the nucleic acid sequence of an antigen binding moiety operably linked to the nucleic acid sequence of an intracellular domain. An exemplary intracellular domain that can be used in the CAR of the invention includes but is not limited to the intracellular domain of CD3-zeta, CD27, CD137, CD28 and the like. In some instances, the CAR can further comprise the apoptosis inducing gene Casp9.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lenti viral vectors have the added advantage over vectors derived from onco-retroviruses such as murine leukemia viruses in that they can transduce non-proliferating cells, such as hepatocytes. They also have the added advantage of low immunogenicity. In another embodiment, the desired CAR can be expressed in the cells by way of transponsons.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence. The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In some embodiments, the genetically modified T cells of the invention are modified through the introduction of RNA. In one embodiment, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, the template for the RNA CAR comprises an extracellular domain comprising an anti-CD19 scFv; a transmembrane domain (such as the hinge and transmembrane domain of CD8a or transmembrane domain of CD28); and a cytoplasmic domain comprises the signaling domain of CD3-zeta and the signaling domain of CD28, CD137 and CD27.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, t is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art.

"Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270: 1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination.

Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7: 1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the CAR sequences (e.g., nucleic acid sequences encoding a CAR as described herein) are delivered into cells using a retroviral or lenti viral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In another embodiment, the desired CAR can be expressed in the cells by way of transponsons.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: an RNA transgene can be delivered to a lymphocyte and expressed therein following a brief in vitro cell activation, as a minimal expressing cassette without the need for any additional viral sequences. Under these conditions, integration of the transgene into the host cell genome is unlikely.

Cloning of cells is not necessary because of the efficiency of transfection of the RNA and its ability to uniformly modify the entire lymphocyte population. Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some WT vectors are known in the literature which are utilized in a standardized manner as template for in vitro transcription and which have been genetically modified in such a way that stabilized RNA transcripts are produced.

Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841 A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro.

Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification of the T cells of the invention, a source of T cells may be obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD1 1b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$.

Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8$^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen. In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, Cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, 10$^4$ to 10$^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFp, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (¾, CD4+) that is greater than the cytotoxic or suppressor T cell population ($T_c$, CD8+). Ex vivo expansion of T cells by stimulating CD3 and CD28 receptors produces a population of T cells that prior to about days 8-9 consists predominately of ¾ cells, while after about days 8-9, the population of T cells comprises an increasingly greater population of Tc cells. Accordingly, depending on the purpose of treatment, infusing a subject with a T cell population comprising predominately of $T_H$ cells may be advantageous. Similarly, if an antigen-specific subset of Tc cells has been isolated it may be beneficial to expand this subset to a greater degree.

Further, in addition to CD4 and CD 8 markers, other phenotypic markers vary significantly, but in large part, reproducibly during the course of the cell expansion process. Thus, such reproducibility enables the ability to tailor an activated T cell product for specific purposes.

Therapeutic Application

In some embodiments, the present invention encompasses a cell (e.g., T cell) modified to express a CAR that combines an antigen recognition domain of a specific antibody with an intracellular domain of CD3-zeta, CD28, CD27, or any combinations thereof. Therefore, in some instances, the transduced T cell can elicit a CAR-mediated T-cell response.

In some embodiments, the invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3-zeta, and a costimulatory signaling region. In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In some embodiments, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, CD19-specific CAR T cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, CD19-specific CAR T cells elicit an immune response specific against cells expressing CD19.

While the data disclosed herein specifically disclose lentiviral vector comprising human anti-CD19 scFv (e.g. C4 scFv), a transmembrane domain, and CD28, CD137, CD27 and CD3-zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer.

In some embodiments, the antigen bind moiety portion of the CAR of the invention is designed to treat a particular cancer. For example, the CAR may be designed to target FRa with the signaling domains CD28, CD137, CD27 and CD3-zeta can be used to treat cancers and disorders including but are not limited to ovarian cancer, lung cancer, breast cancer, renal cancer, colorectal cancer, other solid cancers and the like. As noted above, a CAR designed to target CD19 can be used to treat cancers such as B-cell related cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells. In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of ovarian cancer. In certain embodiments, the cells of the invention are used in the treatment of patients at risk for developing ovarian cancer. Thus, the present invention provides methods for the treatment or prevention of ovarian cancer comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766). Strategies for CAR T cell dosing and scheduling have been discussed (Ertl et al, 2011, Cancer Res, 71:3175-81; Junghans, 2010, Journal of Translational Medicine, 8:55).

Experimental Examples

Aspects of the invention are further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: CAR T Cell Engineering Targeting B Cell Malignancies

FIGS. 1-17 set forth a number of examples showing data that demonstrates a CAR embodiment can be used to treat and effectively cure B-cell malignancies. The data is described further below.

The limitation of adoptive T cell therapy is MHC restriction. Tumors escape by deletion of MHC-I and MHC-II to evade CD8 and CD4 T cells, respectively. Three keys to CAR-T therapy include (a) identifying target antigen and obtaining scFv (b) high efficiency gene transfer into T cells and (c) improved T cell signaling and expansion for efficacy and safety.

Figure 2:
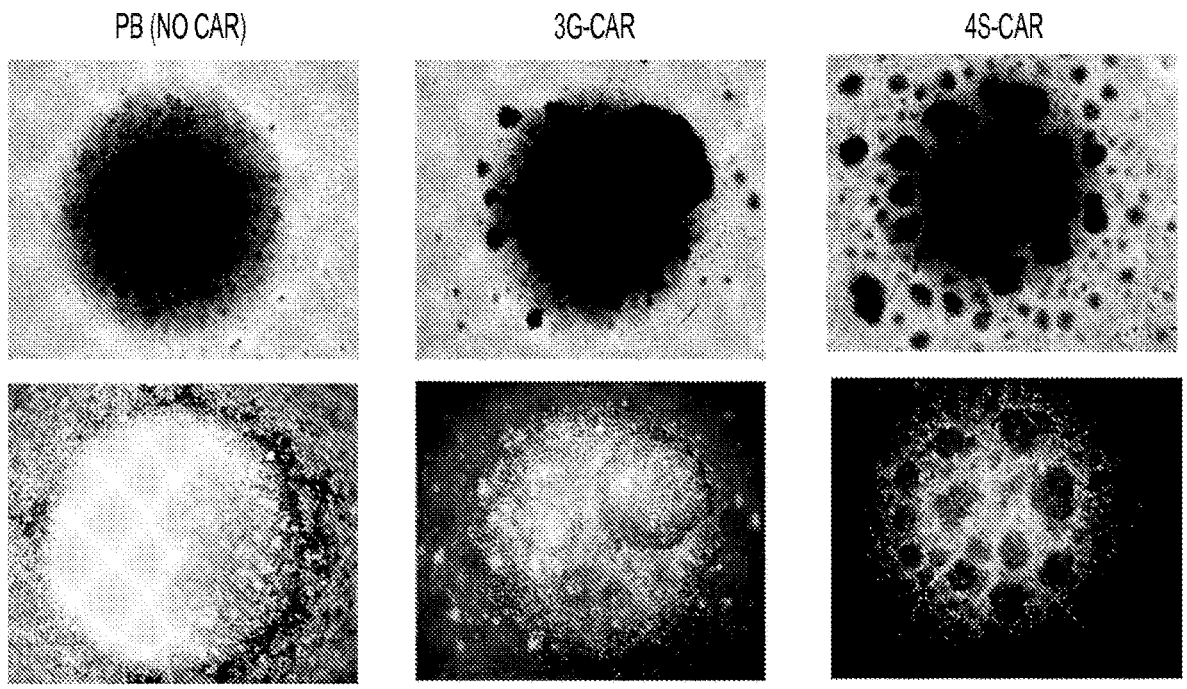
FIG. 2 is a series of photographs that show CAR T cells target GFP+/B-ALL cells. The top row shows brightfield images. The bottom row shows GFP images.
Figure 3:
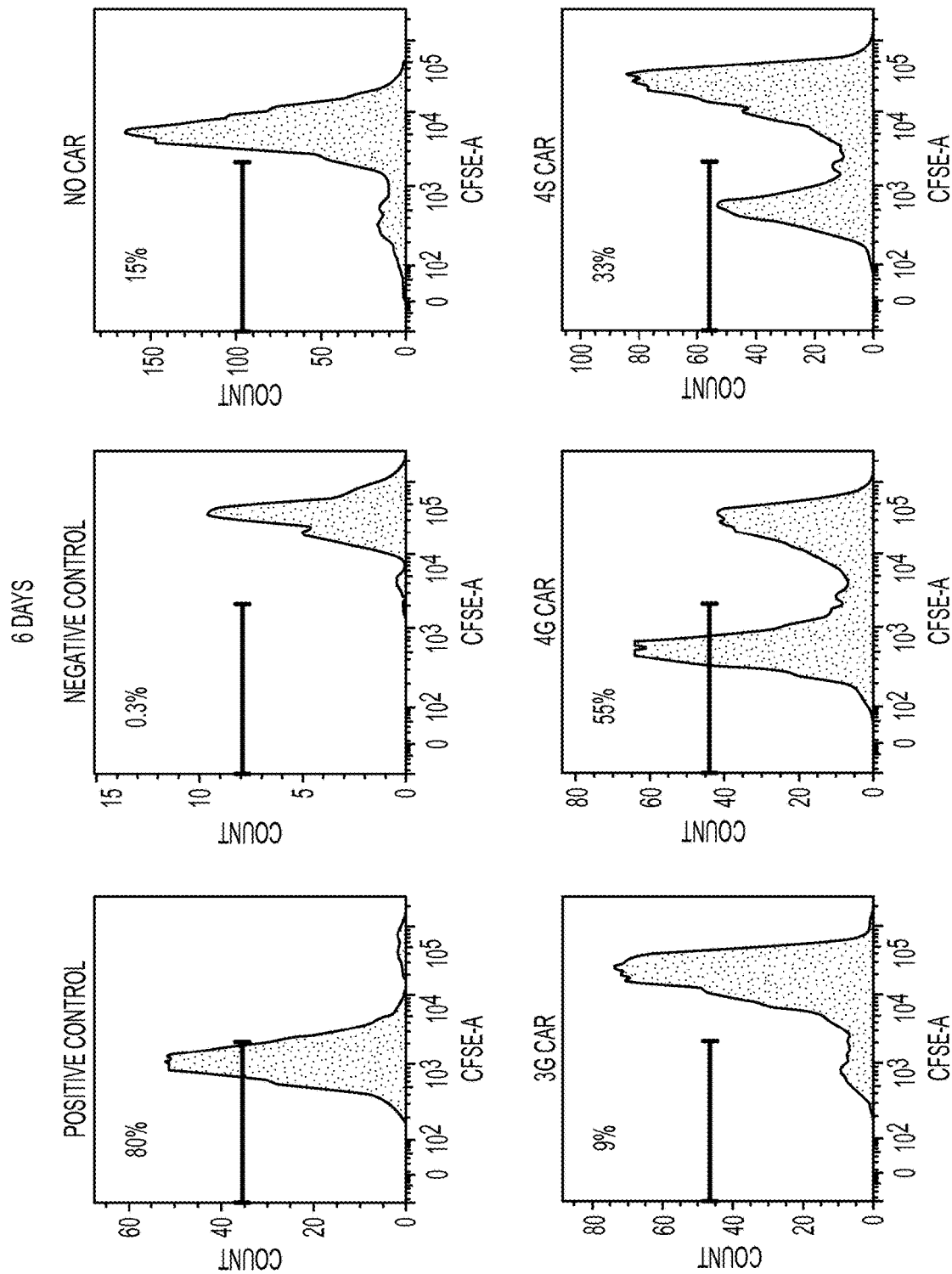
FIG. 3 is a series of graphs depicting a CAR T (CFSE) Proliferation Assay.
Figure 4:
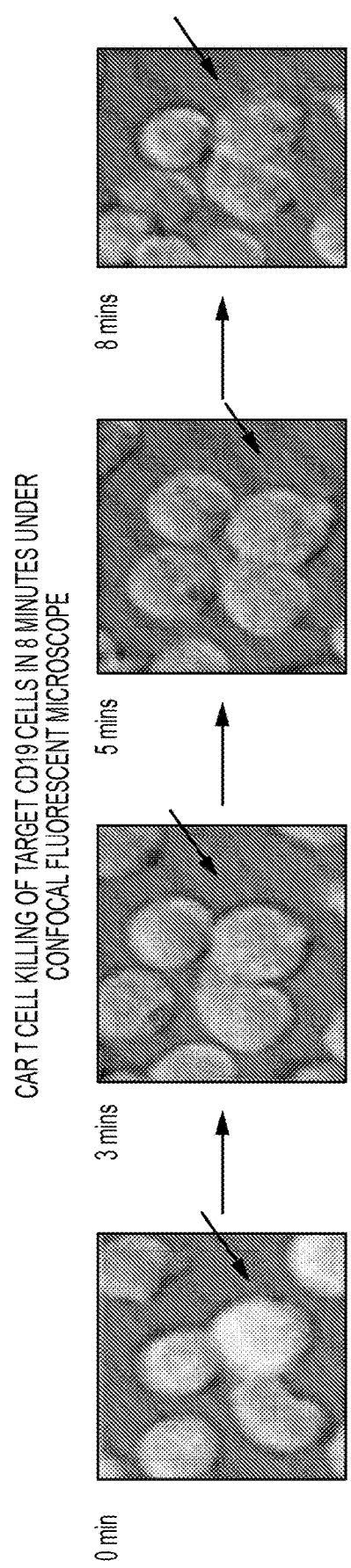
FIG. 4 is a series of photographs showing confocal microscopy imaging of CAR T cells targeting CD19+ cancer cells. The arrow points to a CD19 leukemic cell that is intact at 0 minutes and apoptotic at 8 minutes. The cell adjacent to and to the left of the leukemic cell is an anti-CD19 CAR T cell.

It may be advantageous to use lentiviral vector to deliver CARs to T cells for the following reasons:
  a) Easy to prepare
  b) Large payload, >9 kb
  c) Integrate into dividing and non-dividing cells
  d) Expanded tropism (VSV-G)
  e) No viral genes expressed
  f) No viral promoter (SIN—self inactivated)
  g) No report of HIV-integration related cancer in immunodeficiency (AIDS) patients A CAR-4S lentivector was created (FIG. 1). The CAR-4S included scFv-CD28-CD137-CD27-CD3z-2A-iCasp9. The scFV used was an anti-CD19 scFV. The other domains were added to assist with co-signaling, T cell survival, T cell memory, effector activation and induced safety. The CAR was delivered to T cells and shown to target B-ALL cells (FIG. 2). A CAR T proliferation assay was performed and it was shown that the 4S CAR had a value of 33% at 6 days (FIG. 3). The anti-CD19 CAR T cells were demonstrated to be capable of killing target CD19 leukemic cells, in some cases inducing apoptosis within 8 minutes (FIG. 4).

Figure 5:
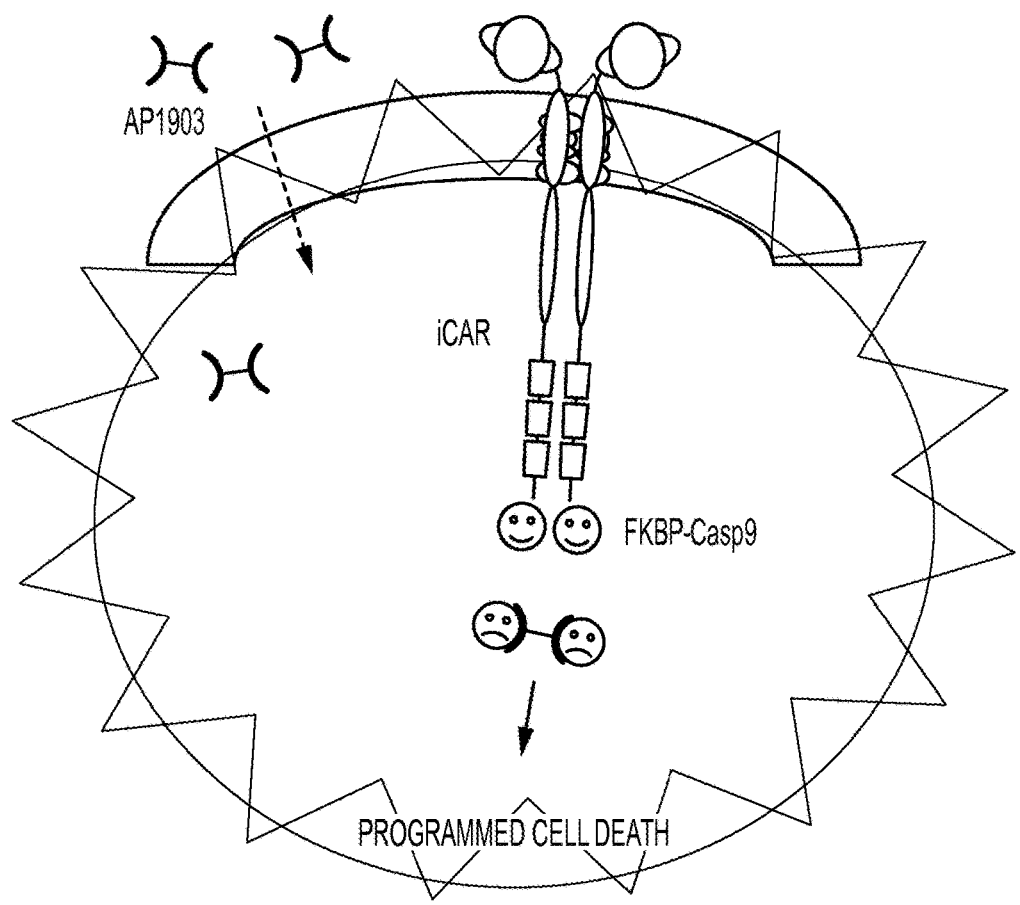
FIG. 5 is a diagram showing a synthetic inducer of CAR dimerization and apoptosis.
Figure 6:
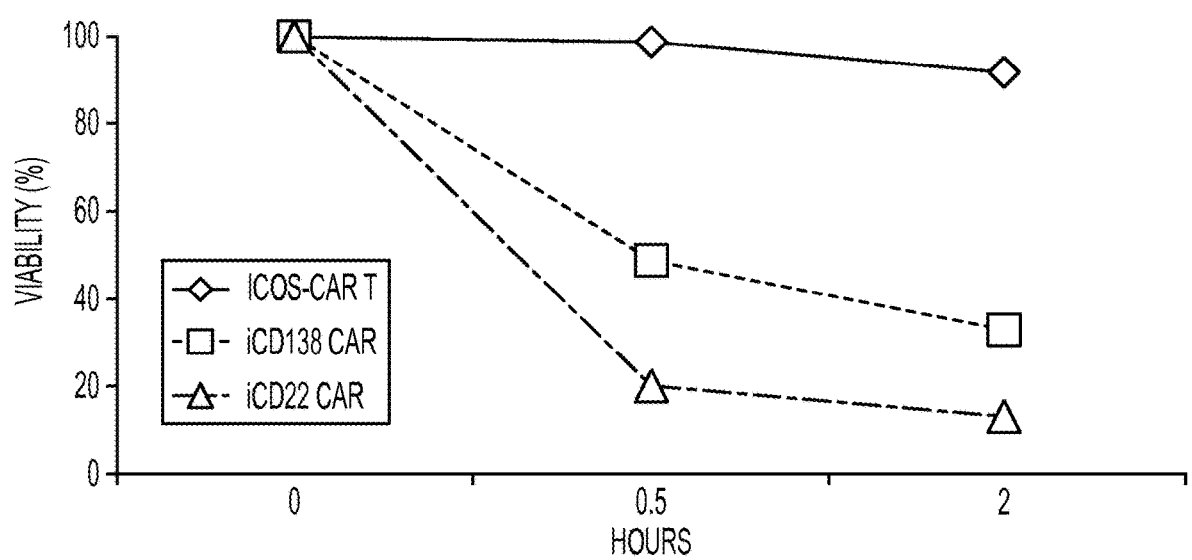
FIG. 6 is a graph showing rapid induction of CAR T apoptosis.
Figure 7:
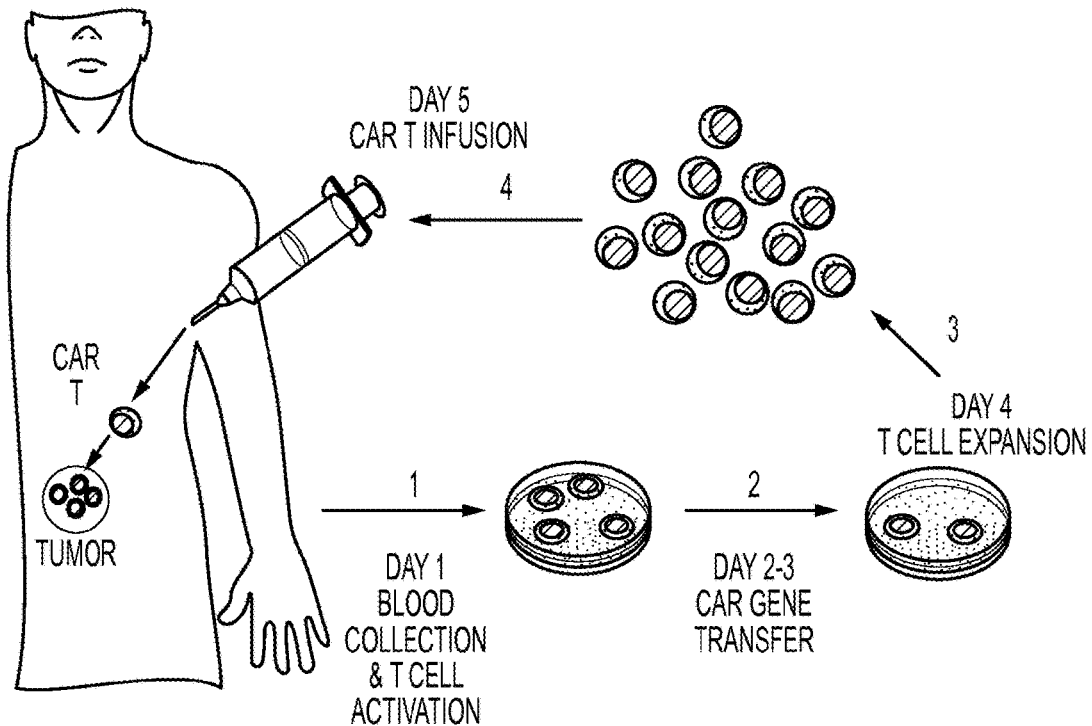
FIG. 7 is a diagram showing Lenti-4S-CAR T cell therapy.
Figure 8:
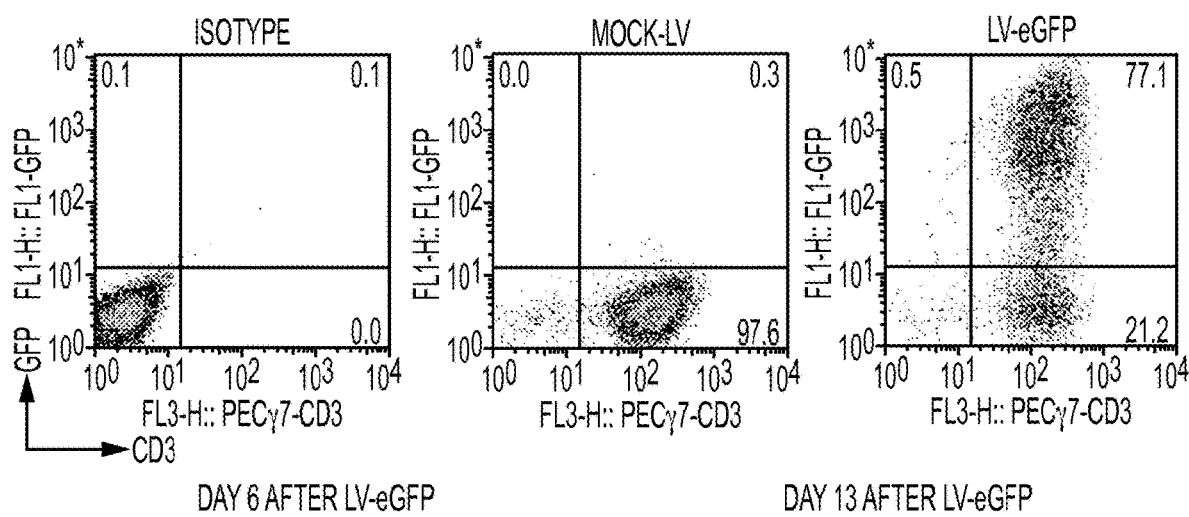
FIG. 8 is a series of graphs of FACS data showing efficient lentiviral (LV) gene transfer into human T cells.
Figure 9:
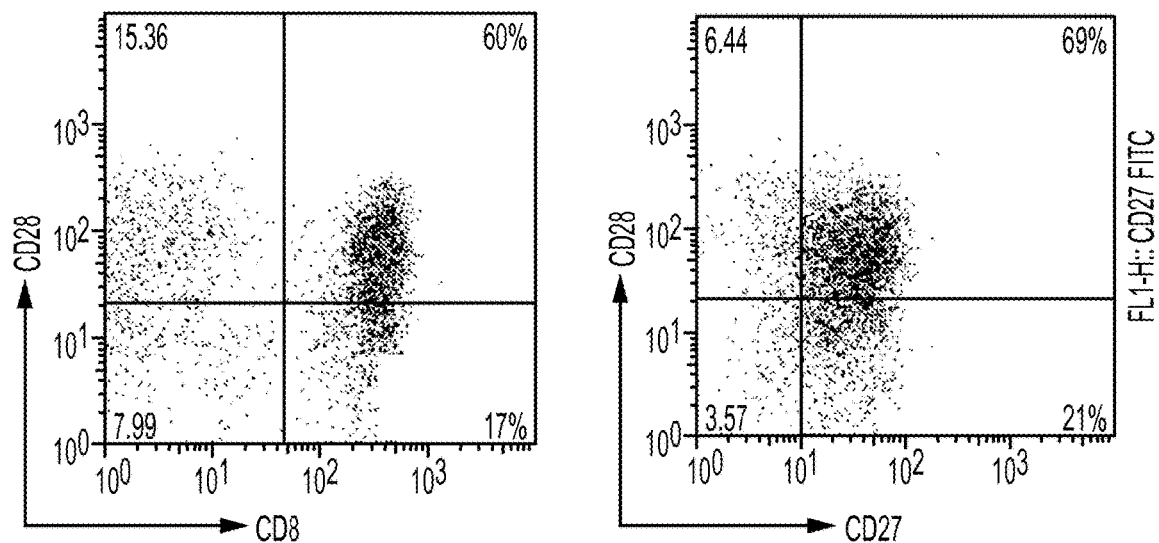
FIG. 9 is a series of graphs of FACS data showing day 5 LV CAR T cells.

To improve the safety of CARs, a synthetic inducer of CAR dimerization and apoptosis can be used, such as AP1903, which can interact with a FKBp-Casp9 (FIG. 5). Such "safety" CARs include 4S-CARs. Apoptosis can be rapidly induced in 4S-CAR T cells (FIG. 6). These 4S-CARs may be used in lenti-4S-CAR T cell therapy, such as by collecting blood and activating T cells on day 1, performed CAR gene transfer on days 2-3, expanding the CAR T cells on day 4, and infusing CAR T cells into a human on day 5 to target a tumor in the human (FIG. 7). As a proof-of-concept, it was shown that lentiviral (LV) gene transfer into human T cells was efficient (FIG. 8). It was shown that these LV CAR T cells expressed CD28 and CD8 or CD28 and CD27 on day 5 post gene transfer (FIG. 9).

Next, two case studies were performed on human patients. The details of the case study 1 patient are below:
  a) 43 yr old Female—relapsed-refractory Ph+ ALL
  b) 8-2007 diagnosed, hyper-CVAD: CR
  c) 11-2007 allo-HSCT
  d) BCR/ABL+: Gleevec
  e) BCR/ABL>125%
  f) ALL relapsed, imatinib resistant
  g) Oral dasatinib, VDLD+IL-2/thymosin
  h) Nilotinib resistant
  i) Ponatinib trial, relapsed BCR/ABL
  j) Relapsed (BM 35%)

Figure 10:
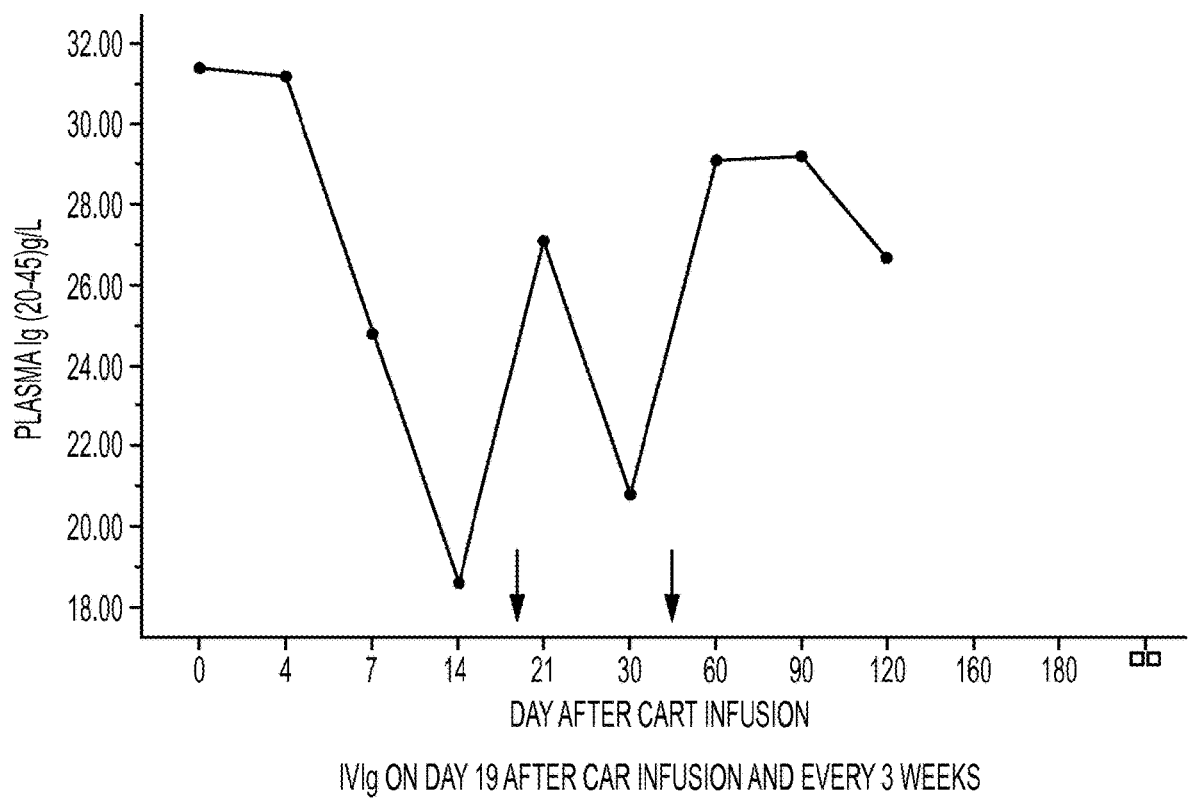
FIG. 10 is a graph showing plasma IgG post CAR-T infusion.
Figure 11:
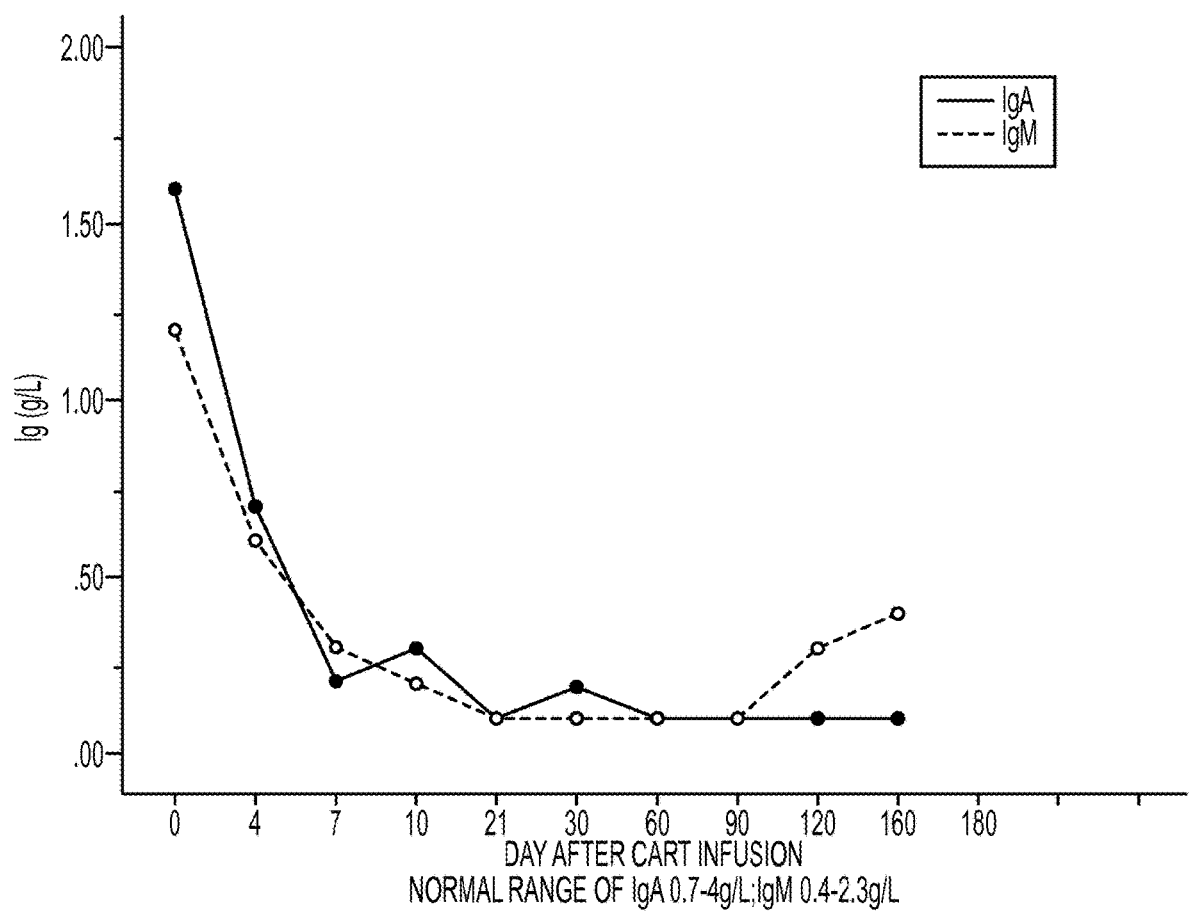
FIG. 11 is a graph showing plasma IgA/IgM post CAR-T infusion.
Figure 12:
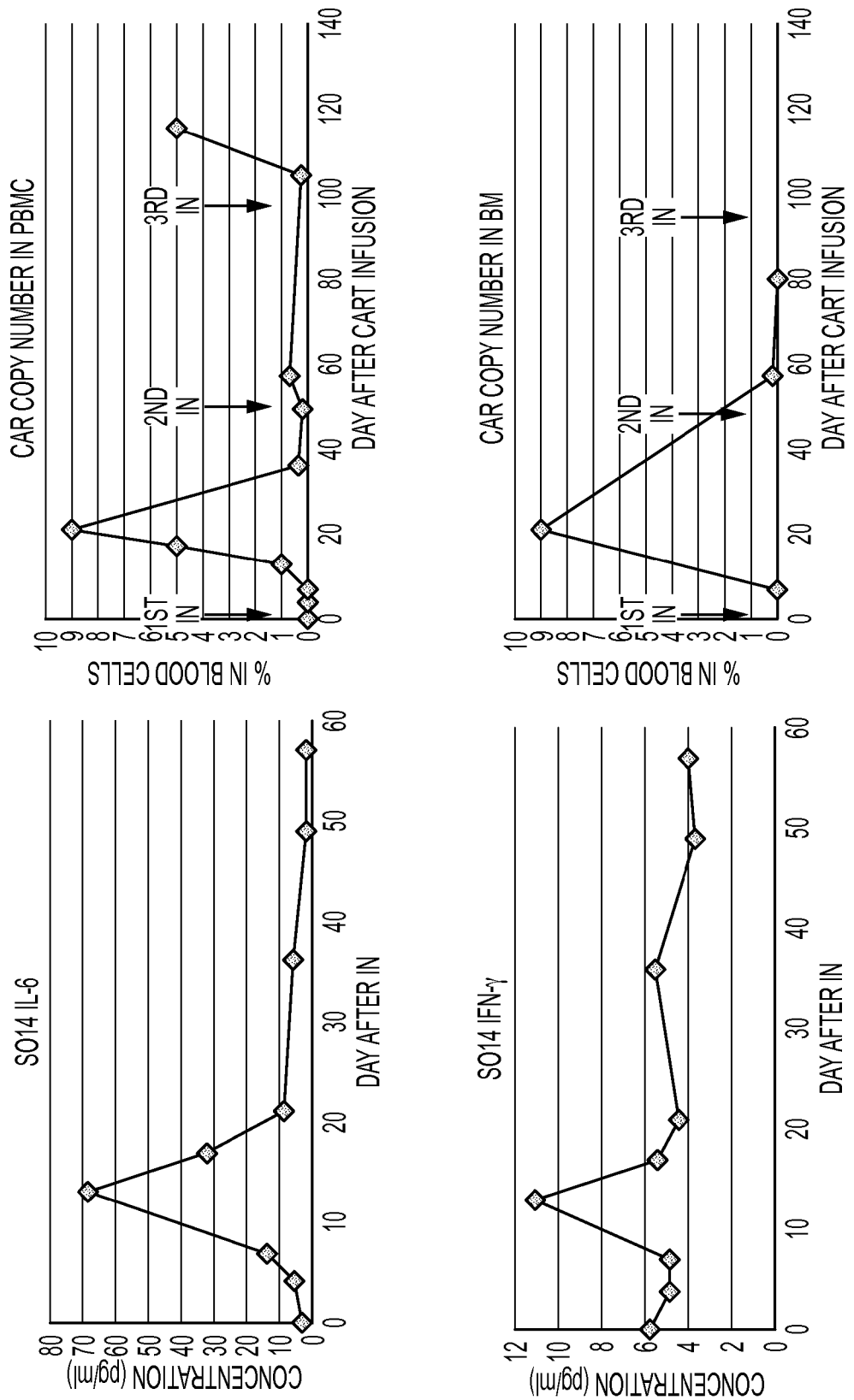
FIG. 12 is a series of graphs showing concentration of IL-6, concentration of IFN-γ, CAR copy number in PBMC, and CAR copy number in BM.
Figure 13:
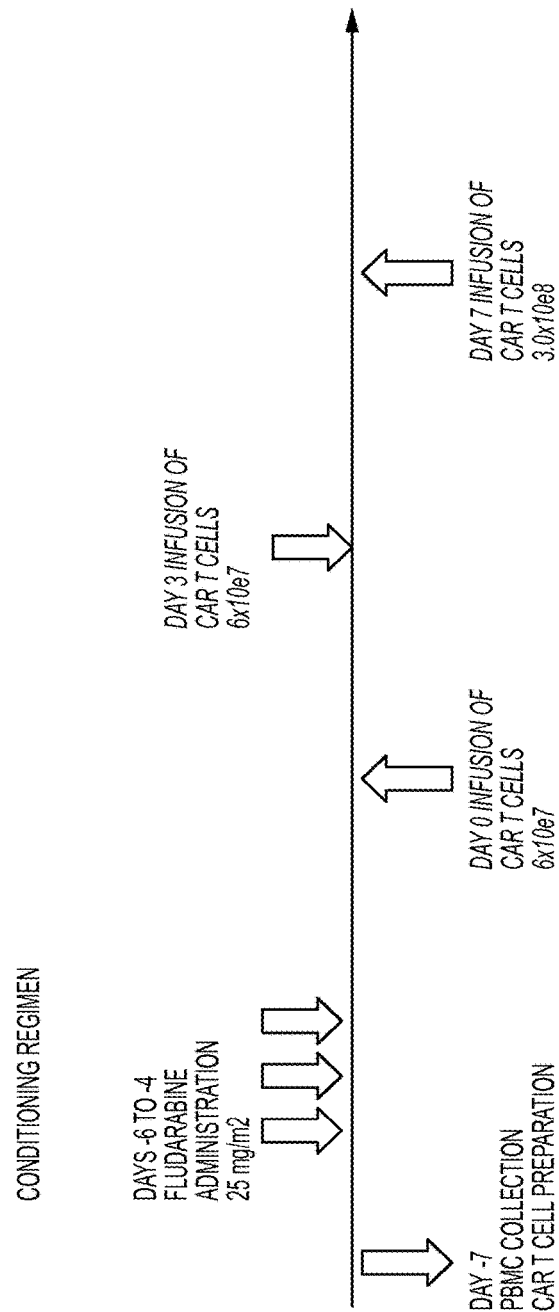
FIG. 13 is a diagram of the treatment protocol used for case study 2.
Figure 14:
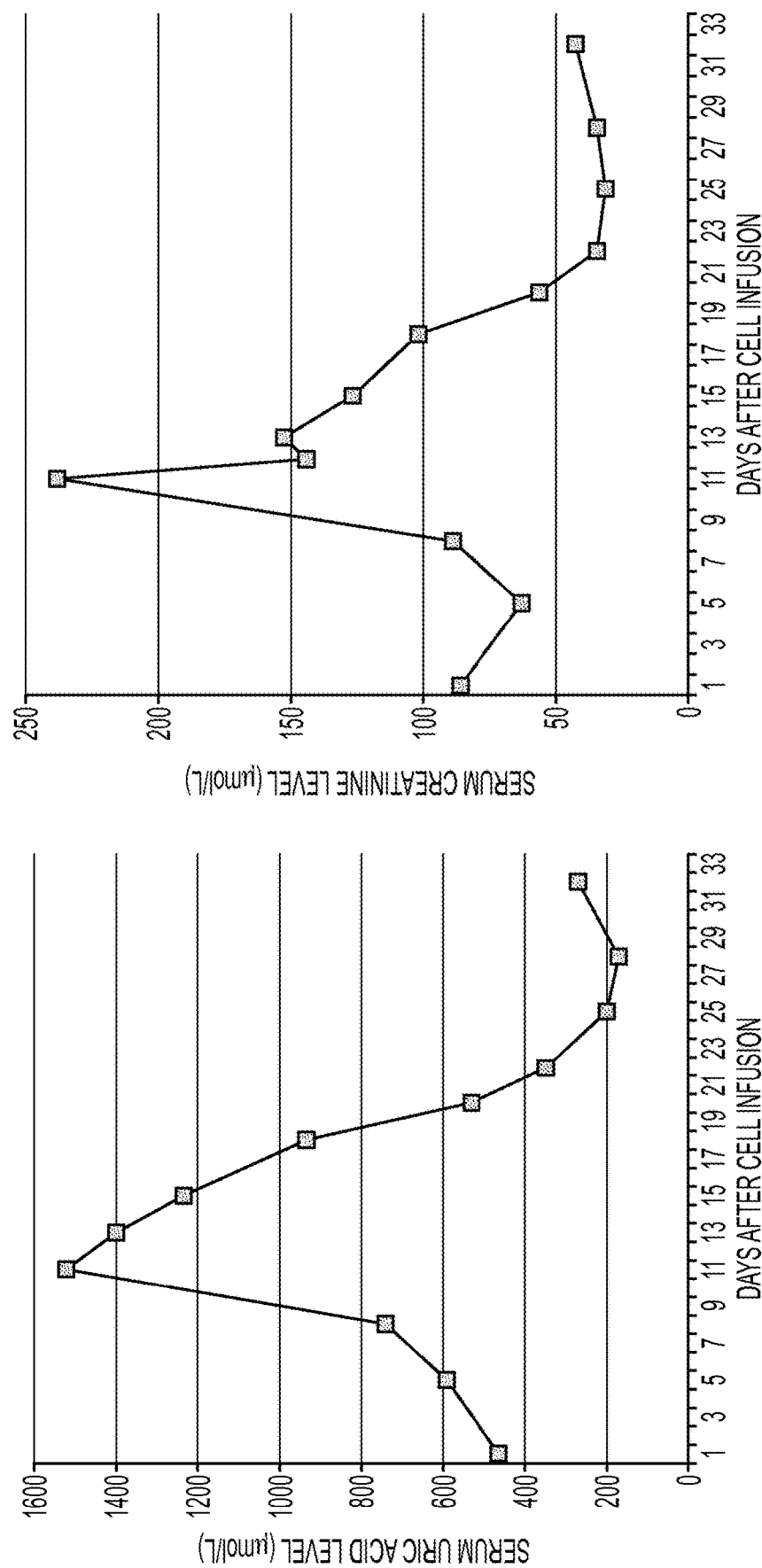
FIG. 14 is a series of graphs showing serum Uric Acid and Creatinine levels at different time points after infusion.

The case study 1 patient received a CD19 CAR T infusion of $1.1 \times 10^8$. The CAR T infusion response at 7 days post infusion included a fever (39.7 C), chest tightness, shortness of breath and coughing with bloody sputum. At 9 days post infusion, the patient had a fever (40C, non-infectious fever) and elevated LDH (1333 U/L vs. normal 114-240 U/L). Plasma IgG was monitored post CAR-T infusion and IVIg was administered to the patient on day 19 after CAR infusion and every 3 weeks thereafter (FIG. 10). Plasma IgA/IgM levels were also monitored post CAR-T infusion (FIG. 11). The case study continued with 3 total infusions: 0.6-3×10e7/kg. The patient was BCR/ABL negative at day 120. The levels of IL-6, interferon-gamma, CAR copy number in peripheral blood mononuclear cells (PBMCs), and CAR copy number in bone marrow (BM) was monitored (FIG. 12).

A second case study (case study 2) was performed. The details of the case study 2 patient are provided below:
a) 34-year-old male
b) Presented with 2 wk history of abdominal mass
c) Biopsy: NHL, Burkitt's lymphoma
   a. IHC: CD20(+++), PAX-5(+++), CD79a(+++), CD10 (+), Bcl-6(+), Mum-1(−), Ki-67(+>75%)
   b. FISH: Myc translocation The treatment history of the case study 2 patient is shown in the table below.

|  | Regimen | Response |
| --- | --- | --- |
| June to August | R-CHOP × 3 | PR |
| September to December | Hyper CVAD (A + B) × 2 | PD |
| January | ICE × 1 | PD |
| February | GEMOX × 1 | PD |

Figure 15:
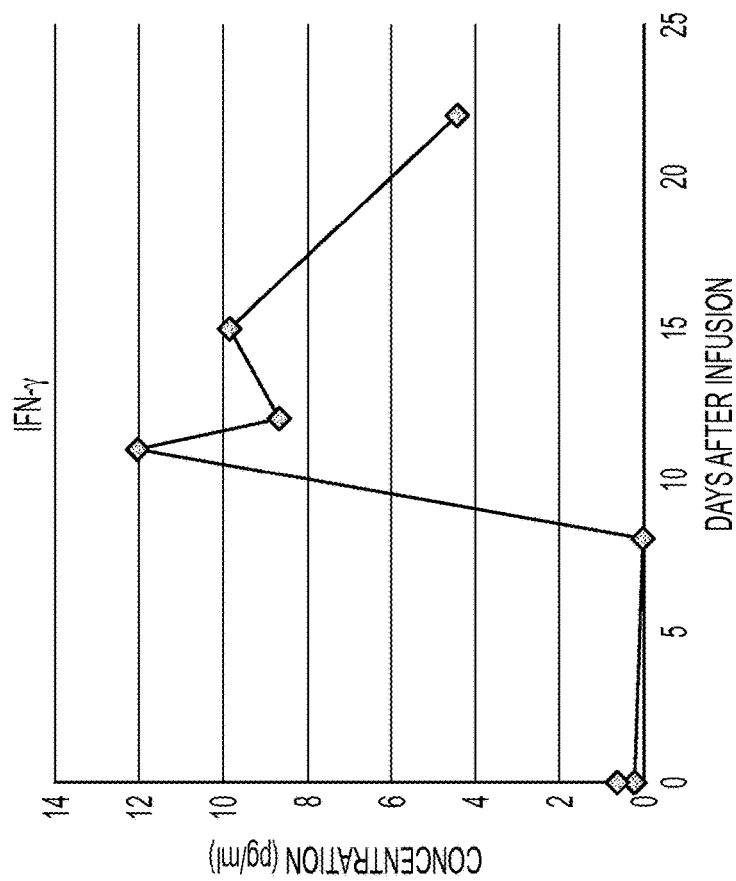
FIG. 15 is a series of graphs showing serum IL-6 and IFN-γ concentrations at different time points after infusion.
Figure 15:
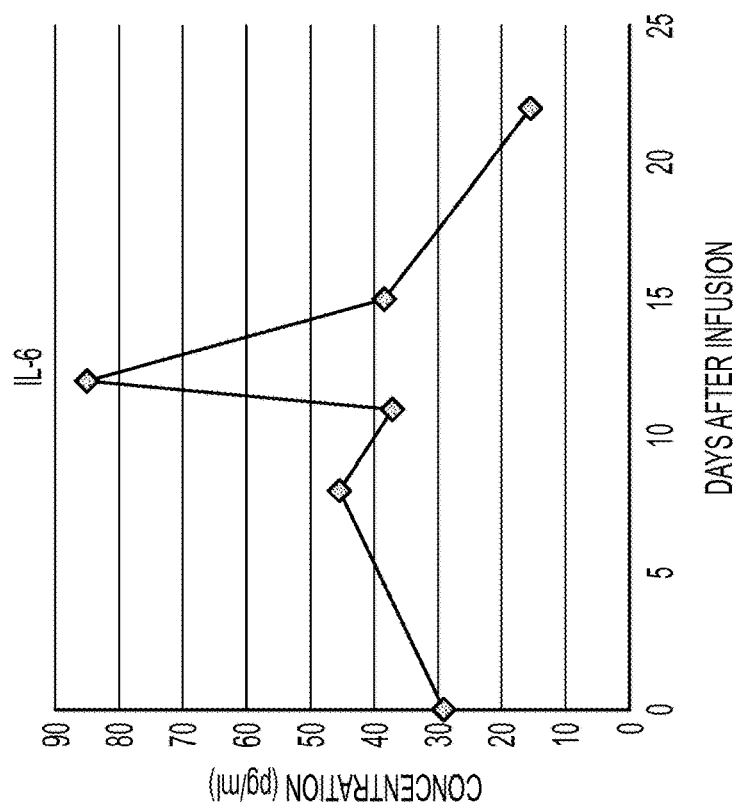
Figure 16:
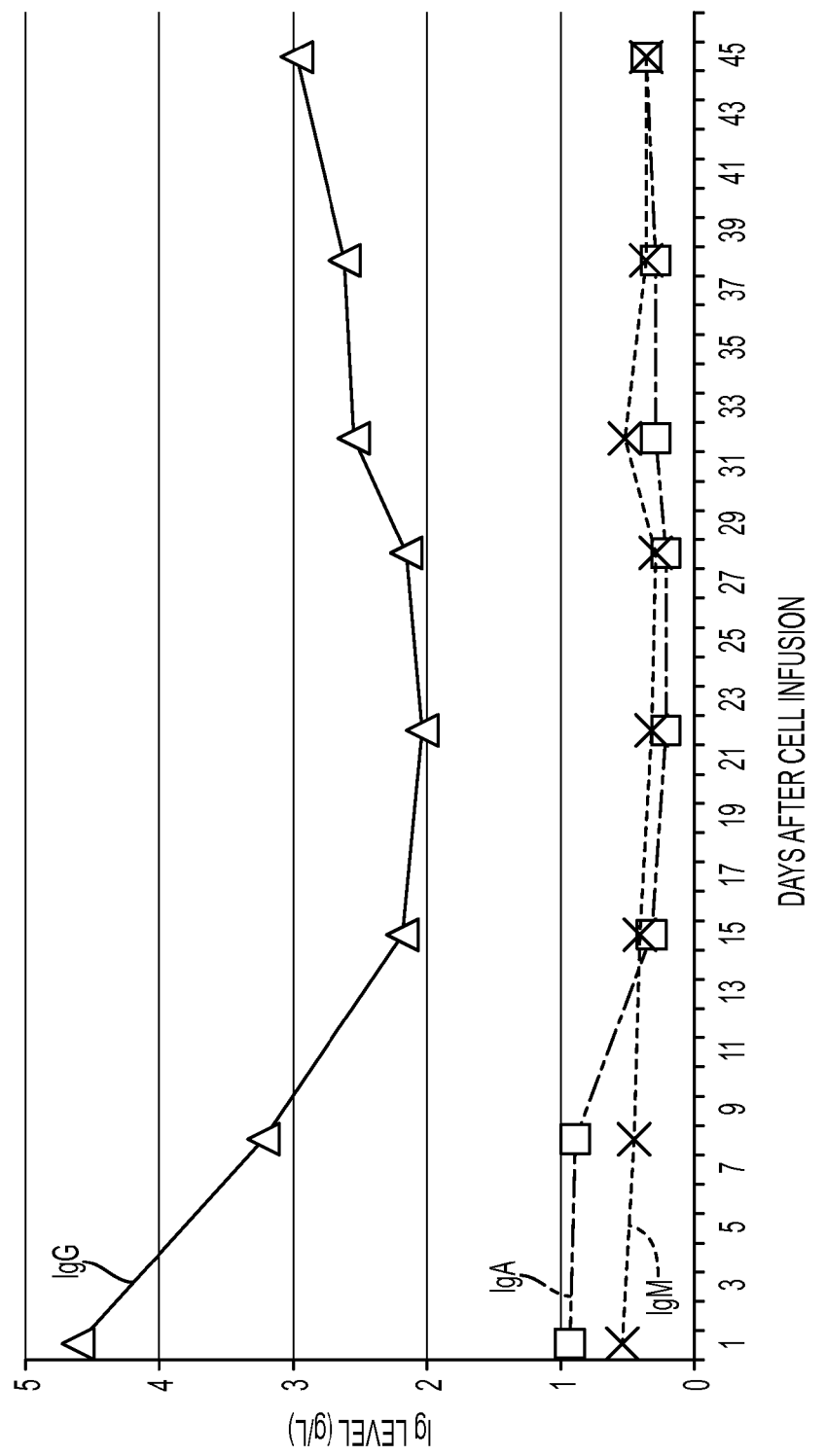
FIG. 16 is a graph showing Ig (IgG, IgA, or IgM) levels at different time points after infusion.
Figure 17:
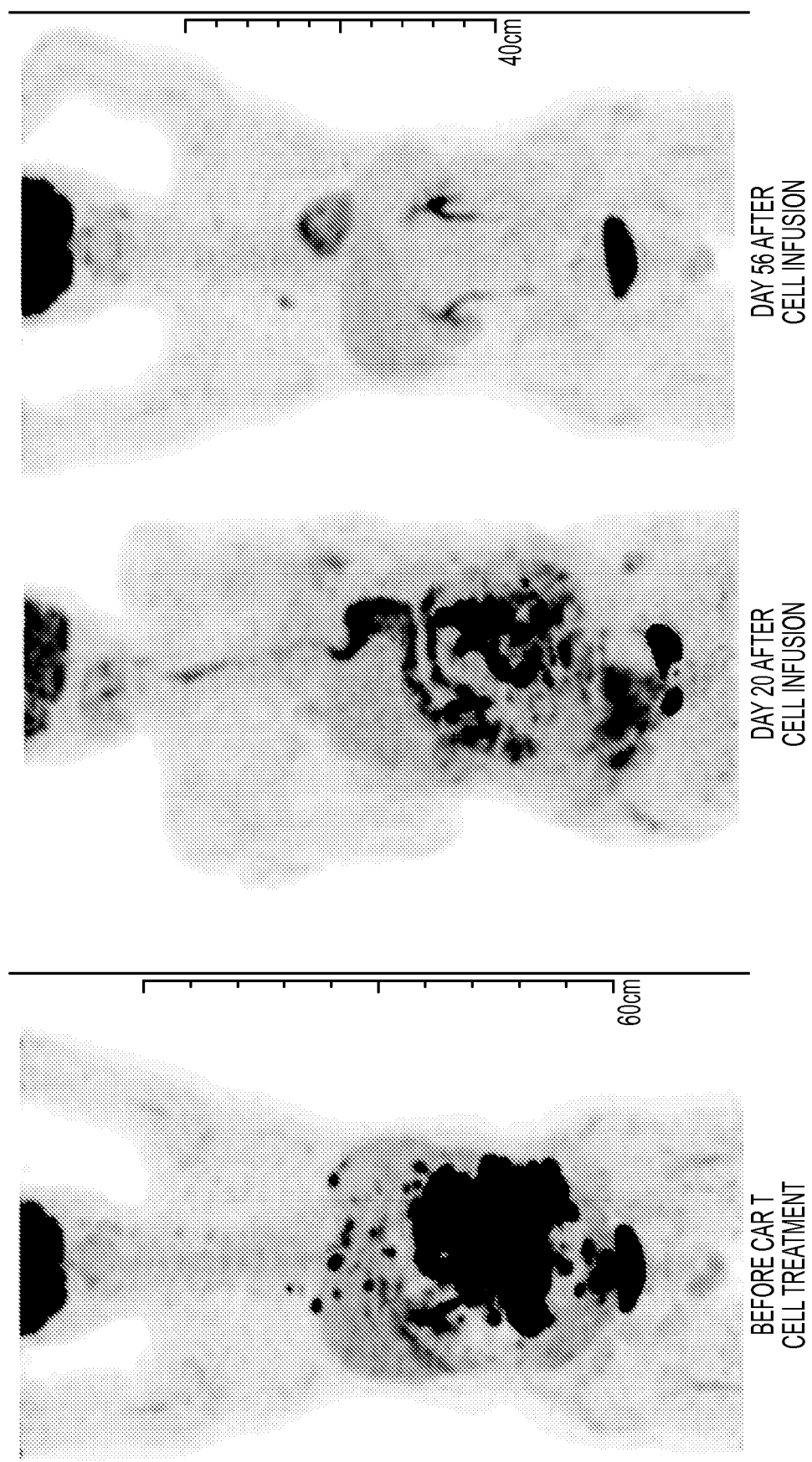
FIG. 17 is a series of photographs showing clinical response, before CAR T cell treatment, 20 days after cell infusion, and 56 days after cell infusion.

The CAR T cell infusion treatment protocol for the patient in case study 2 included PBMC collection and CAR T cell preparation at day −7, fludarabine administration (25 mg/m2) on days −6 to −4, infusion of CAR T cells (6×10e7) on day 8, infusion of CAR T cells (6×10e7) on day 3, and infusion of CAR T cells (3.0×10e8) on day 7. The infusion response on day 11 included:

a) Diaphoresis, anorexia, nausea, vomiting, hypoxia
b) Fever: 39.3° C.
c) Hypotension: BP 75/45 mmHg
d) HR: 150-180 bpm
e) Fluid resuscitation, infusion of dopamine The serum uric acid and creatine levels of the patient were also monitored (FIG. 14), as were the level of serum cytokines IL-6 and interferon-gamma (FIG. 15). The levels of IgG, IgA, and IgM were also monitored (FIG. 16). The clinical response of the patient was also monitored, and B cell reduction was observed (FIG. 17).

In summary, 4S generation CAR T cells targeted B-ALL with high efficiency, CAR T cells rapidly expanded and eradicated B cells in vivo, infused CAR T cells were capable of quickly reaching BM, and the 4S CAR design was an important safety feature in patients.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

What is claimed is:

1. A chimeric antigen receptor (CAR) comprising an antigen binding domain, a transmembrane domain, a costimulatory signaling region, and a CD3 zeta signaling domain, wherein the costimulatory signaling region consists essentially of a CD28 signaling domain, a CD137 signaling domain and a CD27 signaling domain, wherein the antigen binding domain is an scFv, wherein the CAR further comprises a 2A peptide linker and an iCasp9 domain, and wherein the CAR is arranged as follows:

scFv-CD28-CD137-CD27-CD3z-2A-iCasp9.

2. The CAR of claim 1, wherein the antigen binding domain binds to a tumor antigen, wherein the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, and MAGE A3 TCR, or any combination thereof.

3. The CAR of claim 2, wherein the tumor antigen is CD19.

4. An isolated nucleic acid encoding the chimeric antigen receptor (CAR) of claim 1.

5. The isolated nucleic acid of claim 1, wherein the sequence is codon-optimized for expression in human cells.

6. A vector comprising the isolated nucleic acid of claim 1.

7. A cell comprising the chimeric antigen receptor (CAR) of claim 1.

8. The cell of claim 7, wherein the cell is selected from the group consisting of a T cell, a Natural Killer (NK) cell, a cytotoxic T lymphocyte (CTL), and a regulatory T cell.

* * * * *